(12) United States Patent
Kim

(10) Patent No.: US 12,354,526 B2
(45) Date of Patent: Jul. 8, 2025

(54) DISPLAY DEVICE TO MEASURE BLOOD PRESSURE

(71) Applicant: SAMSUNG DISPLAY CO., LTD., Yongin-si (KR)

(72) Inventor: Chul Kim, Yongin-si (KR)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 155 days.

(21) Appl. No.: 18/170,647

(22) Filed: Feb. 17, 2023

(65) Prior Publication Data
US 2024/0000389 A1 Jan. 4, 2024

(30) Foreign Application Priority Data

Jun. 29, 2022 (KR) .......................... 10-2022-0079719

(51) Int. Cl.
*G09G 3/32* (2016.01)
*G06F 3/041* (2006.01)
(Continued)

(52) U.S. Cl.
CPC ............. *G09G 3/32* (2013.01); *G06F 3/0412* (2013.01); *G06F 3/0414* (2013.01);
(Continued)

(58) Field of Classification Search
CPC .... G09G 3/32–3291; G09G 2300/0842–0866; G09G 2354/00;
(Continued)

(56) References Cited

U.S. PATENT DOCUMENTS 10,537,792 B1 * 1/2020 Harte ...................... A63F 13/35
10,885,304 B2 * 1/2021 Huang ............... G06V 40/1306
(Continued)

FOREIGN PATENT DOCUMENTS

EP 3342336 7/2018
EP 3469984 4/2019
(Continued)

OTHER PUBLICATIONS

Extended European Search Report dated Dec. 5, 2023 in corresponding EP Appln. No. 23180874.2-1113.

*Primary Examiner* — Patrick F Marinelli
(74) *Attorney, Agent, or Firm* — F. CHAU & ASSOCIATES, LLC

(57) ABSTRACT

A display device includes display pixels having light emitting elements arranged in a display area of a display panel and pixel drivers connected to the light emitting elements, light sensing pixels having light sensing elements arranged in the display area and sensing drivers connected to the light sensing elements, a display scan driver configured to sequentially supply display scan signals to the pixel drivers, a light sensing driver configured to sequentially supply sensing scan signals to the sensing drivers, a blood pressure detection circuit configured to measure a blood pressure of a user using light sensing signals received from the sensing drivers, and a display driving circuit configured to supply control signals to the display scan driver and the light sensing driver to control a light sensing signal detection timing of the light sensing pixels when a mode of the display device is switched to a blood pressure measurement mode.

20 Claims, 31 Drawing Sheets

(51) Int. Cl.
  *G06F 3/0481* (2022.01)
  *G06F 3/04883* (2022.01)
  *G06V 40/13* (2022.01)
  *G09G 3/20* (2006.01)
  *G09G 3/3233* (2016.01)

(52) U.S. Cl.
  CPC .......... *G06F 3/0416* (2013.01); *G06F 3/0481* (2013.01); *G06F 3/04883* (2013.01); *G06V 40/1318* (2022.01); *G09G 3/2096* (2013.01); *G09G 3/3233* (2013.01); *G09G 2300/0842* (2013.01); *G09G 2354/00* (2013.01); *G09G 2380/08* (2013.01)

(58) Field of Classification Search
  CPC ................ G06F 3/0412; G06F 3/0416; G06F 3/04166–04186; G06F 3/044–0448; G06F 3/048–04883
  See application file for complete search history.

(56) References Cited

U.S. PATENT DOCUMENTS

| | | | | |
|---|---|---|---|---|
| 10,942,995 | B2* | 3/2021 | Won | G09G 5/003 |
| 11,430,360 | B2* | 8/2022 | Lee | G06F 1/1684 |
| 11,507,225 | B2* | 11/2022 | Chen | G06V 40/1335 |
| 11,625,955 | B1* | 4/2023 | Kumar | G06V 40/1306 |
| | | | | 382/126 |
| 11,793,465 | B2* | 10/2023 | Hong | A61B 5/6843 |
| 11,800,342 | B2* | 10/2023 | Sreeram | G06F 3/048 |
| 11,896,397 | B2* | 2/2024 | Kim | A61B 5/02108 |
| 12,014,688 | B2* | 6/2024 | Kim | A61B 5/02141 |
| 12,158,774 | B2* | 12/2024 | Lee | A61B 5/02108 |
| 2014/0028589 | A1* | 1/2014 | Reilly | G06F 21/88 |
| | | | | 345/173 |
| 2016/0063283 | A1* | 3/2016 | Wang | G06F 21/82 |
| | | | | 726/27 |
| 2017/0119307 | A1* | 5/2017 | Shim | A61B 5/7475 |
| 2018/0267659 | A1* | 9/2018 | Huang | G06F 3/04166 |
| 2019/0008399 | A1 | 1/2019 | Mukkamala et al. | |
| 2019/0065717 | A1* | 2/2019 | Won | G06V 40/1318 |
| 2019/0087620 | A1* | 3/2019 | Kim | G09G 3/3233 |
| 2019/0096959 | A1* | 3/2019 | Lee | H10K 59/351 |
| 2019/0102597 | A1* | 4/2019 | Lu | G09G 3/32 |
| 2020/0175143 | A1* | 6/2020 | Lee | G06F 3/0446 |
| 2020/0210677 | A1* | 7/2020 | Huang | G06V 10/147 |
| 2021/0158751 | A1* | 5/2021 | Cha | G06V 10/143 |
| 2021/0307697 | A1* | 10/2021 | Hong | A61B 5/7278 |
| 2021/0319198 | A1* | 10/2021 | Seomoon | G06V 40/1318 |
| 2022/0013598 | A1* | 1/2022 | Park | H10K 59/352 |
| 2022/0130305 | A1* | 4/2022 | Lee | H10F 55/18 |
| 2022/0165834 | A1* | 5/2022 | Jo | H10K 59/60 |
| 2023/0085885 | A1* | 3/2023 | Sreeram | G06V 40/15 |
| | | | | 455/404.1 |
| 2023/0090998 | A1* | 3/2023 | Kumar | G06V 10/993 |
| | | | | 382/126 |
| 2023/0114016 | A1* | 4/2023 | Choi | H10K 59/90 |
| | | | | 600/480 |
| 2023/0165096 | A1* | 5/2023 | Lee | A61B 5/02108 |
| | | | | 345/440.1 |
| 2023/0185333 | A1* | 6/2023 | Lee | A61B 5/02108 |
| | | | | 361/679.01 |
| 2023/0255502 | A1* | 8/2023 | An | A61B 5/02116 |
| | | | | 600/485 |
| 2023/0345775 | A1* | 10/2023 | Lee | G06V 40/1318 |
| 2023/0346315 | A1* | 11/2023 | An | A61B 5/6826 |
| 2023/0363720 | A1* | 11/2023 | Jones | A61B 5/02255 |
| 2023/0377524 | A1* | 11/2023 | Song | G09G 3/3233 |
| 2023/0397885 | A1* | 12/2023 | Kim | G06F 3/0416 |
| 2023/0414119 | A1* | 12/2023 | Kim | A61B 5/02108 |
| 2024/0000389 | A1* | 1/2024 | Kim | G06F 3/0416 |
| 2024/0029658 | A1* | 1/2024 | Kim | A61B 5/0059 |
| 2024/0046869 | A1* | 2/2024 | Kim | A61B 5/443 |
| 2024/0135862 | A1* | 4/2024 | Seo | H10K 59/131 |
| 2024/0273939 | A1* | 8/2024 | Kim | G06V 40/1318 |
| 2024/0295765 | A1* | 9/2024 | Kim | G06V 40/1318 |
| 2024/0296801 | A1* | 9/2024 | Kim | G09G 3/3266 |

FOREIGN PATENT DOCUMENTS

| | | |
|---|---|---|
| EP | 3881756 | 3/2021 |
| EP | 3788950 | 10/2021 |
| KR | 10-2021-0037556 | 4/2021 |
| KR | 10-2021-0043277 | 4/2021 |

\* cited by examiner

USPX: SPX1, SPX2, SPX3, LSP

DA

DISPLAY DEVICE TO MEASURE BLOOD PRESSURE

CROSS-REFERENCE TO RELATED APPLICATION

This U.S. non-provisional patent application claims priority under 35 U.S.C. § 119 to Korean Patent Application No. 10-2022-0079719 filed on Jun. 29, 2022 in the Korean Intellectual Property Office, the disclosure of which is incorporated by reference in its entirety herein.

1. TECHNICAL FIELD

The present disclosure relates to a display device to measure blood pressure.

2. DISCUSSION OF RELATED ART

With the advance of information-oriented society, more and more demands are placed on display devices for displaying images in various ways. The display devices have been applied to various electronic devices, such as a smart phone, a digital camera, a laptop computer, a tablet personal computer (PC), a navigation system, and a smart television. In the case of portable display devices such as a smartphone and a tablet PC, various functions such as image capturing, fingerprint recognition, and face recognition are provided together.

Recently, as the healthcare industry is in the spotlight, methods have been developed to more easily obtain biometric information related to health. For example, attempts have been made to replace a traditional blood pressure measuring device with a portable device that measures blood pressure using an oscillometric technique.

However, such a device requires a separate light source, sensor, and display, and it is inconvenient since it is necessary to separately carry the device in addition to a smartphone or tablet PC.

SUMMARY

Aspects of the present disclosure provide a display device capable of measuring a user's blood pressure by detecting a photoplethysmography signal using a display panel of the display device.

Aspects of the present disclosure also provide a display device capable of measuring blood pressure with only a gentle touch of a surface of a display panel of the display device.

According to an embodiment of the disclosure, a display device includes display pixels having light emitting elements arranged in a display area of a display panel and pixel drivers connected to the light emitting elements, light sensing pixels having light sensing elements arranged in the display area and sensing drivers connected to the light sensing elements, a display scan driver configured to sequentially supply display scan signals to the pixel drivers, a light sensing driver configured to sequentially supply sensing scan signals to the sensing drivers, a blood pressure detection circuit configured to measure a blood pressure of a user using light sensing signals received from the sensing drivers, and a display driving circuit configured to supply control signals to the display scan driver and the light sensing driver to control a light sensing signal detection timing of the light sensing pixels when a mode of the display device is switched to a blood pressure measurement mode.

In an embodiment, the display device further includes a pressure sensing unit disposed on one of a rear surface and a front surface of the display panel to sense pressure applied at a position of the display area by a body part of the user to generate a pressure sensing signal, and a touch driver configured to generate pressure data and pressure sensing coordinate data according to a change in magnitude of the pressure sensing signal and the position.

In an embodiment, the display device further includes a touch sensing unit disposed on the display panel to detect a touch of the user at the position to generate a touch sensing signal, and a touch driver configured to generate touch data and touch coordinate data according to the position and a magnitude change of the touch sensing signal.

In an embodiment, among the display pixels of the display area, red, green, and blue display pixels and one light sensing pixel form each unit pixel, and the red, green, and blue display pixels and the one light sensing pixel are alternately arranged in a horizontal or vertical stripe.

In an embodiment, the display scan driver sequentially supplies display scan signals to the pixel drivers for each horizontal line in response to a write control signal from the display driving circuit, and the light sensing driver sequentially supplies the sensing scan signals to the sensing drivers for each horizontal line in response to a light sensing control signal from the display driving circuit.

In an embodiment, the mode is switched to the blood pressure measurement mode according to a blood pressure measurement function selection operation or an application execution operation by the user, and when switched to the blood pressure measurement mode, preset video data is supplied to the data driver, and the write control signal is supplied to the display scan driver to display information on the display area indicating the switch to the blood pressure measurement mode.

In an embodiment, the display driving circuit displays a guide phrase to inform the user of a switch to the blood pressure measurement mode for inducing the user to touch a touch area of the display area, touch sensing signals are received through the touch sensing unit to detect the touch data and the touch coordinate data, and the touch data and the touch coordinate data are transmitted to the display driving circuit in real time.

In an embodiment, the display driving circuit detects and sets the touch area based on the touch coordinate data, grayscale data preset for blood pressure detection are aligned according to a position of the touch area and supplied to a data driver, and a write control signal is supplied to the display scan driver to control the display pixels of the touch area to emit light, and a light sensing control signal is supplied to the light sensing driver to control the sensing scan signals to be sequentially supplied to the sensing drivers.

In an embodiment, the display driving circuit supplies coordinate information on the touch area to the blood pressure detection circuit, and the blood pressure detection circuit receives the light sensing signals through each sensing driver corresponding to the touch area based on the coordinate information on the touch area and detects a pulse wave signal from the light sensing signals and calculates blood pressure of a user from the pulse wave signal.

In an embodiment, the touch driver transmits pressure data according to a magnitude change of the pressure sensing signals to the display driving circuit, and the display driving circuit controls a data driver and the display scan driver such that a preset pressurization information display image is displayed on the display area through an option, and a pressure change according to the pressure data is displayed as the pressurization information display image in real time.

In an embodiment, the pressurization information display image is displayed in at least one of a bar block type, a bar gauge type, a circular gauge type, a polygonal figure size type, a polygonal figure gauge type, a polygonal figure block type, a bar graph type, or an arrow gauge type.

In an embodiment, when the mode is switched to the blood pressure measurement mode, the display driving circuit randomly presets a size of a touch area to be touched by the user and an arrangement position of the touch area, and driving timings of a data driver and the display scan driver are controlled to display the randomly set touch area and a preset touch inducing image on the display area.

In an embodiment, the display driving circuit aligns image data for displaying the touch inducing image according to the randomly set touch area and supplies the image data to the data driver, and a write control signal is supplied to the display scan driver to control the touch area and the preset touch inducing image to be displayed.

In an embodiment, the display driving circuit aligns grayscale data preset for blood pressure detection in the randomly set touch area according to a position of the touch area and supplies the grayscale data to the data driver, the write control signal is supplied to the display scan driver to control the display pixels of the touch area to emit light, and the light sensing control signal is supplied to the light sensing driver to control the sensing scan signals to be sequentially supplied to the sensing drivers.

In an embodiment, the display driving circuit supplies coordinate information on the randomly set touch area to the blood pressure detection circuit, and the blood pressure detection circuit receives the light sensing signals through each sensing driver corresponding to the touch area based on the coordinate information on the touch area, detects a pulse wave signal from the light sensing signals and calculates blood pressure of the user from the pulse wave signal.

In an embodiment, when the mode is switched to the blood pressure measurement mode, the display driving circuit randomly converts and sets a size of a touch area to be touched by the user and an arrangement position of the touch area, and driving timings of the data driver and the display scan driver are controlled to display boundary lines of the randomly set touch area on the display area.

In an embodiment, when the mode is switched to the blood pressure measurement mode, the touch driver receives pressure sensing signals in real time through the pressure sensing unit to detect pressure data and pressure sensing coordinate data, the pressure data and the pressure sensing coordinate data detected in real time are transmitted to the display driving circuit, and the display driving circuit sets a touch area to be touched by the user based on the pressure data and the pressure sensing coordinate data.

In an embodiment, the display driving circuit aligns image data for displaying the touch area set by the pressure sensing coordinate data according to the touch area and supplies the image data to a data driver, and a write control signal is supplied to the display scan driver to control a touch inducing image of the touch area set by the pressure sensing coordinate data to be displayed.

In an embodiment, the display driving circuit aligns grayscale data preset for blood pressure detection through the touch area set by the pressure sensing coordinate data according to a position of the touch area and supplies the grayscale data to the data driver, the write control signal is supplied to the display scan driver to control the display pixels of the touch area to emit light, and the light sensing control signal is supplied to the light sensing driver to control the sensing scan signals to be sequentially supplied to the sensing drivers.

In an embodiment, the display driving circuit supplies coordinate information on the touch area set by the pressure sensing coordinate data to the blood pressure detection circuit, and the blood pressure detection circuit receives the light sensing signals through each sensing driver corresponding to the touch area based on the coordinate information on the touch area, detects a pulse wave signal from the light sensing signals and calculates blood pressure of the user from the pulse wave signal.

According to an embodiment of the disclosure, a display device including display pixels having light emitting elements arranged in a display area of a display panel and pixel drivers connected to the light emitting elements, light sensing pixels having light sensing elements arranged in the display area and sensing drivers connected to the light sensing elements, a display scan driver configured to sequentially supply display scan signals to the pixel drivers, a light sensing driver configured to sequentially supply sensing scan signals to the sensing drivers, a blood pressure detection circuit configured to measure a blood pressure of a user using light sensing signals received from the sensing drivers, a display driving circuit configured to supply control signals to the display scan driver and the light sensing driver to control a light sensing signal detection timing of the light sensing pixels when a mode of the display device is switched to a blood pressure measurement mode, a pressure sensing unit disposed on the display panel to sense pressure applied during a touch by a body part of the user on a position of the display area to generate a pressure sensing signal, a touch sensing unit disposed on the display panel to detect the touch to generate a touch sensing signal, and a touch driver configured to generate pressure data, coordinate and touch data according to the position, a magnitude change of the pressure sensing signal, and a magnitude change of the touch sensing signal.

In a display device according to at least one embodiment, when light emitted from an image display pixel is reflected by a specific body part such as user's finger blood vessels, the reflected light is sensed in a light sensing pixel of the display panel, so that the user's blood pressure may be detected. Accordingly, the user's blood pressure may be detected using the display panel of the display device.

In a display device according to at least one embodiment, even if the user lightly touches a position on the image display surface of the display panel, the user's touch position may be sensed, so that the user's blood pressure may be measured. Accordingly, the user may measure the blood pressure by comfortably touching the display panel without checking a designated touch location or the like.

BRIEF DESCRIPTION OF THE DRAWINGS

The above and other aspects and features of the present disclosure will become more apparent by describing in detail embodiments thereof with reference to the attached drawings, in which.

DETAILED DESCRIPTION OF THE EMBODIMENTS

The present invention will now be described more fully hereinafter with reference to the accompanying drawings, in which example embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

It will also be understood that when a layer is referred to as being "on" another layer or substrate, it can be directly on the other layer or substrate, or intervening layers may also be present. The same reference numbers indicate the same components throughout the specification.

It will be understood that, although the terms "first," "second," etc. may be used herein to describe various elements, these elements should not be limited by these terms. These terms are only used to distinguish one element from another element. For instance, a first element discussed below could be termed a second element without departing from the teachings of the present invention. Similarly, the second element could also be termed the first element.

Each of the features of the various embodiments of the present disclosure may be combined or combined with each other, in part or in whole, and technically various interlocking and driving are possible. Each embodiment may be implemented independently of each other or may be implemented together in an association.

Hereinafter, illustrative embodiments will be described in detail with reference to the accompanying drawings.

Figure 1:
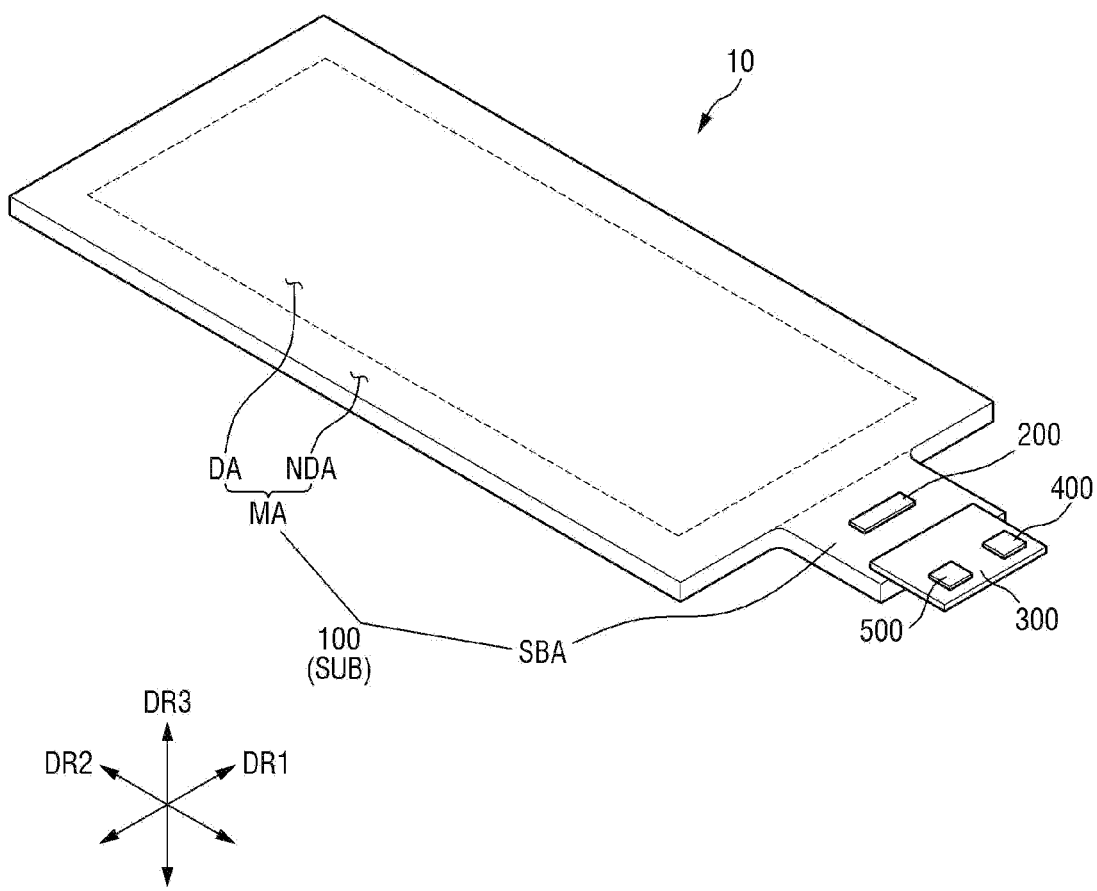
FIG. 1 is a perspective view illustrating a display device according to an embodiment.
Figure 2:
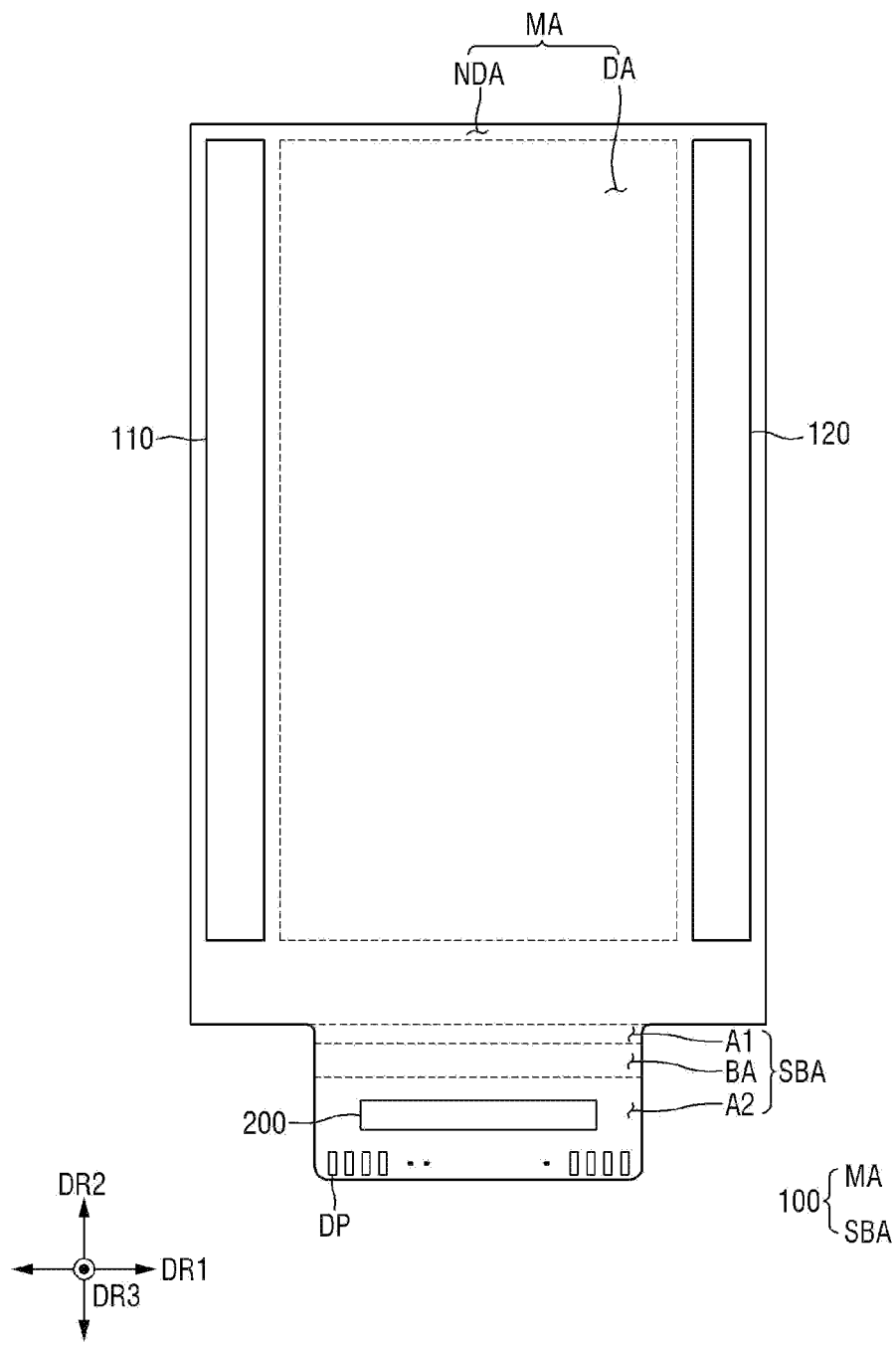
FIG. 2 is a plan view illustrating an arrangement structure of a display panel and a display driving circuit shown in FIG. 1.
Figure 3:
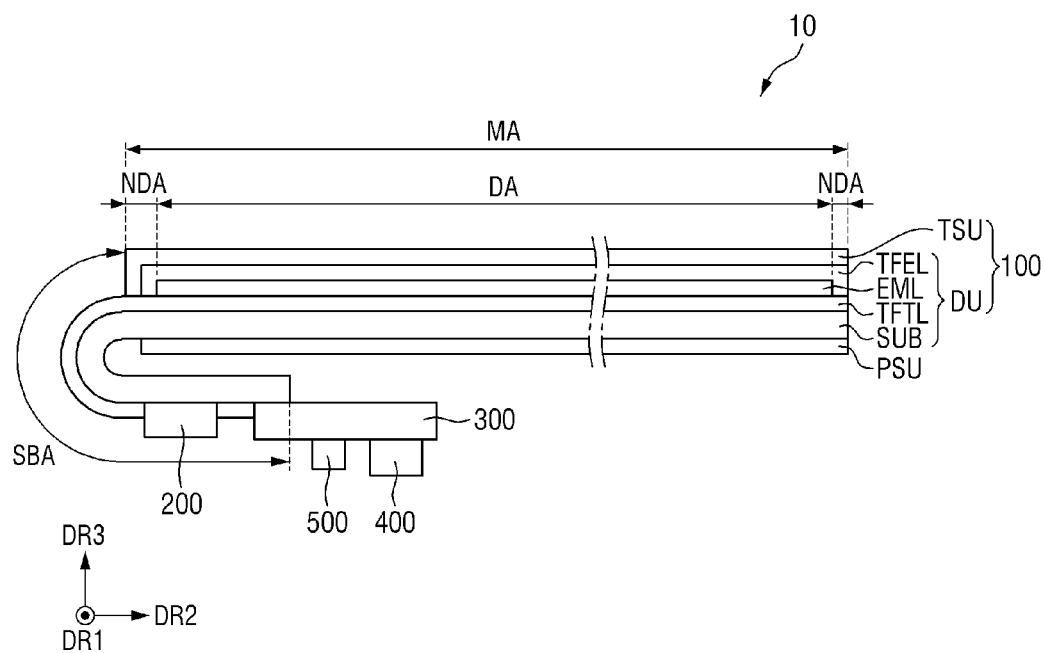
FIG. 3 is a cross-sectional view specifically showing the configuration of the display device shown in FIG. 1.

FIG. 1 is a perspective view illustrating a display device according to an embodiment. FIG. 2 is a plan view illustrating an arrangement structure of a display panel and a display driving circuit shown in FIG. 1. FIG. 3 is a cross-sectional view specifically showing the configuration of the display device shown in FIG. 1.

First of all, referring to FIGS. 1 and 2, a display device 10 according to an embodiment may be applied to portable electronic devices such as a mobile phone, a smartphone, a tablet personal computer, a mobile communication terminal, an electronic organizer, an electronic book, a portable multimedia player (PMP), a navigation system, an ultra mobile PC (UMPC) or the like. Alternatively, the display device 10 according to an embodiment may be applied as a display unit of a television, a laptop, a monitor, a billboard, or an Internet-of-Things (IoT) terminal. Alternatively, the display device 10 according to an embodiment may be applied to wearable devices such as a smart watch, a watch phone, a glasses type display, or a head mounted display (HMD). Alternatively, the display device 10 according to an embodiment may be applied to a dashboard of a vehicle, a center fascia of a vehicle, a center information display (CID) disposed on a dashboard of a vehicle, a room mirror display in place of side mirrors of a vehicle, or a display disposed on a rear surface of a front seat for rear seat entertainment of a vehicle.

The display device 10 may be a light emitting display device such as an organic light emitting display using an organic light emitting diode, a quantum dot light emitting display including a quantum dot light emitting layer, an inorganic light emitting display including an inorganic semiconductor, and a micro light emitting display using a micro or nano light emitting diode (LED). In the following description, it is assumed that the display device 10 is an organic light emitting display device, but the present disclosure is not limited thereto.

Referring to FIGS. 1 and 3, the display device 10 includes a display panel 100, a display driving circuit 200, a circuit board 300, a blood pressure detection circuit 400, and a touch driver 500. The display panel 100 may include a touch sensing unit TSU (e.g., a touch sensor), a display unit DU, and a pressure sensing unit PSU. The display unit DU may include a substrate SUB, a thin film transistor layer TFTL, a light emitting element layer EML, and an encapsulation layer TFEL.

The substrate SUB may be a base substrate or a base member. The substrate SUB may be a flexible substrate that may be bent, folded, rolled, or the like. For example, the substrate SUB may include a glass material or a metal material, but is not limited thereto. As another example, the substrate SUB may include a polymer resin such as polyimide PI.

The thin film transistor layer TFTL may be disposed on the substrate SUB. The thin film transistor layer TFTL may include a plurality of thin film transistors constituting a pixel circuit of pixels. The thin film transistor layer TFTL may further include gate lines, data lines, power lines, and gate control lines.

The display panel 100 may, in a plan view, be formed in a rectangular shape having short sides in a first direction DR1 and long sides in a second direction DR2 crossing the first direction DR1. A corner where the short side in the first direction DR1 and the long side in the second direction DR2 meet may be right-angled or rounded to have a predetermined curvature. The planar shape of the display panel 100 is not limited to the rectangular shape, and may be formed in another polygonal shape, a circular shape or an elliptical shape. The display panel 100 may be formed to be flat, but is not limited thereto. For example, the display panel 100 may include a curved portion formed at left and right ends and having a predetermined curvature or a varying curvature. In addition, the display panel 100 may be formed flexibly so that it can be curved, bent, folded, or rolled.

The substrate SUB of the display panel 100 may include a main region MA and a sub-region SBA.

The main region MA may include a display area DA displaying an image and a non-display area NDA that is a peripheral area of the display area DA.

The non-display area NDA may be disposed adjacent to the display area DA. The non-display area NDA may be an area outside the display area DA. The non-display area NDA may be disposed to surround the display area DA. The non-display area NDA may be an edge area of the display panel 100.

The display area DA includes display pixels for displaying an image, and light sensing pixels for sensing light reflected from a user's body part such as a finger. The display area DA may occupy most of the main region MA. The display area DA may be disposed at the center of the main region MA.

The display area DA may be divided into an image display region in which only the display pixels are disposed without the light sensing pixels, and a blood pressure detection region in which both the display pixels and the light sensing pixels are disposed. In other words, the light sensing pixels may be disposed together with the display pixels only in a preset blood pressure detection region which is a part of the entire display area DA of the display panel 100. However, an example in which the display pixels and the light sensing pixels are alternately arranged in the entire display area DA will be described below.

Referring to FIGS. 2 and 3, the sub-region SBA may protrude from one side of the main region MA in the second direction DR2. The length of the sub-region SBA in the second direction DR2 may be less than the length of the main region MA in the second direction DR2. The length of the sub-region SBA in the first direction DR1 may be substantially equal to or less than the length of the main region MA in the first direction DR1.

The sub-region SBA may include a first region A1, a second region A2, and a bending area BA.

The first area A1 is a region protruding from one side of the main region MA in the second direction DR2. One side of the first region A1 may be in contact with the non-display area NDA of the main region MA, and the other side of the first region A1 may be in contact with the bending area BA.

The second area A2 is an area on which pads DP and the display driving circuit 200 are disposed. The display driving circuit 200 may be attached to driving pads of the second area A2 using a conductive adhesive member such as an anisotropic conductive film. The circuit board 300 may be attached to the pads DP of the second area A2 using a conductive adhesive member. One side of the second region A2 may be in contact with the bending area BA.

The bending area BA is an area capable of being bent. When the bending area BA is bent, the second region A2 may be disposed under the first region A1 and under the main region MA. The bending area BA may be disposed between the first region A1 and the second region A2. One side of the bending area BA may be in contact with the first region A1, and the other side of the bending area BA may be in contact with the second region A2.

As shown in FIG. 3, the sub-region SBA may be bent, and in this case, it may be disposed under the main region MA. The sub-region SBA may overlap the main region MA in a third direction DR3.

The touch sensing unit TSU for sensing a body part such as a finger is formed or disposed on the front portion of the display panel 100. The touch sensing unit TSU may include a plurality of touch electrodes to sense a user's touch in a capacitance manner.

The touch sensing unit TSU may include a plurality of touch electrodes arranged to intersect each other in the first and second directions DR1 and DR2. In an embodiment, the plurality of touch electrodes include a plurality of driving electrodes arranged to be spaced apart from each other in parallel in the first direction DR1, and a plurality of sensing electrodes arranged to be spaced apart from each other in parallel in the second direction DR2 so as to intersect the plurality of driving electrodes with an organic material layer or an inorganic material layer interposed therebetween. The plurality of driving electrodes and the plurality of sensing electrodes may be formed to extend to a wiring region between display pixels SPX and light sensing pixels LSP arranged in the display area DA so as not to overlap the display pixels and the light sensing pixels. The plurality of driving electrodes and the plurality of sensing electrodes may form mutual capacitance to transmit touch sensing signals that varies depending on a user's touch to the touch driver 500.

The touch driver 500 may supply touch driving signals to the plurality of driving electrodes and may receive the touch sensing signals from the plurality of sensing electrodes. The touch driver 500 may sense a change in mutual capacitance between the plurality of driving electrodes TE and the plurality of sensing electrodes depending on a change in the magnitude of the touch sensing signal. In addition, the touch driver 500 may supply touch data according to a change in the mutual capacitance, coordinate data of a position where the touch is sensed, and the like to the display driving circuit 200.

A pressure sensing unit PSU for sensing a pressure applied by a body part such as a finger may be disposed or formed on the rear surface of the display panel 100, e.g., on the rear surface of the substrate SUB. The pressure sensing unit PSU may be formed in a transparent sheet type in which a plurality of transparent electrodes are arranged in vertical and horizontal directions, and may be disposed on the front surface of the main region MA. Alternatively, the pressure sensing unit PSU may be disposed or formed on the front surface of the display panel 100.

In an embodiment, the pressure sensing unit PSU includes a plurality of pressure sensing electrodes arranged to intersect each other in the first and second directions DR1 and DR2. In an embodiment, the plurality of pressure sensing electrodes include a plurality of lower electrodes arranged to be spaced apart from each other in parallel in the first direction DR1, and a plurality of upper electrodes arranged to be spaced apart from each other in parallel in the second direction DR2 so as to intersect the plurality of lower electrodes with a transparent inorganic (or organic) material layer interposed therebetween. The plurality of lower electrodes and the plurality of upper electrodes may form a self-capacitance with a transparent inorganic (or organic) material layer interposed therebetween, and transmit pressure sensing signals that vary depending on a user's touch pressure to the touch driver 500. The arrangement structure and detailed structure of the pressure sensing unit PSU will be described later in more detail with reference to the accompanying drawings.

Figure 4:
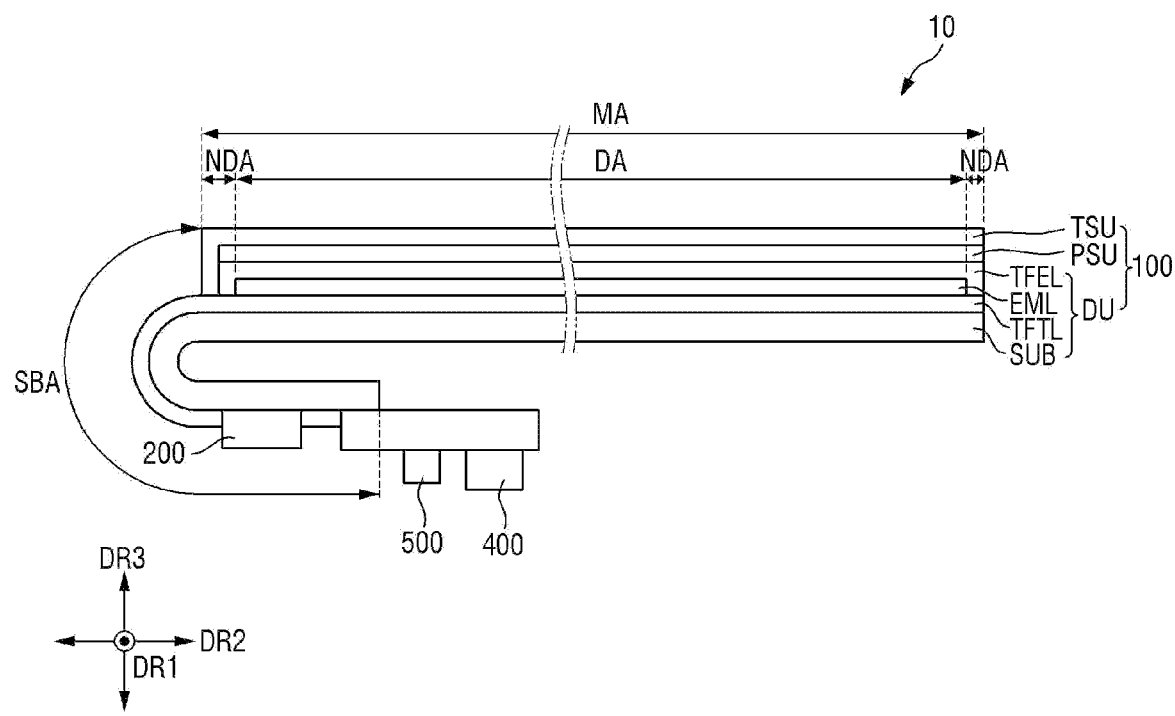
FIG. 4 is a cross-sectional view of an embodiment illustrating the configuration of the display device shown in FIG. 1.

FIG. 4 is a cross-sectional view of an embodiment illustrating the configuration of the display device shown in FIG. 1.

FIG. 4 illustrates an example in which the pressure sensing unit PSU is disposed on the front surface of the display panel 100, e.g., on a surface between the display panel 100 and the touch sensing unit TSU.

When the pressure sensing unit PSU is disposed on the front surface of the display panel 100, pressure sensing electrodes, i.e., a plurality of lower electrodes and a plurality of upper electrodes, of the pressure sensing unit PSU may be formed to extend to the wiring region between the display pixels and the light sensing pixels arranged in the display area DA so as not to overlap the display pixels and the light sensing pixels. The pressure sensing electrodes transmit the pressure sensing signals that vary depending on the user's touch pressure to the touch driver 500. The detailed structure of the pressure sensing electrodes will be described later with reference to the accompanying drawings.

Meanwhile, the touch driver 500 may receive the pressure sensing signals from the plurality of lower electrodes or the plurality of upper electrodes, and may sense a change in self-capacitance through the pressure sensing signals. Accordingly, the touch driver 500 may supply pressure data according to the amount of change in the self-capacitance, sensing coordinate data of a position where the pressure is sensed, and the like to the display driving circuit 200.

The circuit board 300 may be attached to one end of the sub-region SBA. Thus, the circuit board 300 may be electrically connected to the display panel 100 and the display driving circuit 200. The display panel 100 and the display driving circuit 200 may receive digital video data, timing signals, and driving voltages through the circuit board 300. The circuit board 300 may be a flexible printed circuit board, a printed circuit board, or a flexible film such as a chip on film.

The display driving circuit 200 may generate control signals and electrical signals for driving the display panel 100. Each of the display driving circuit 200, the blood pressure detection circuit 400, and the touch driver 500 may be formed of an integrated circuit (IC), and may be attached onto the display panel 100 or the circuit board 300 by a chip on glass (COG) method, a chip on plastic (COP) method, or an ultrasonic bonding method, but is not limited thereto. For example, the display driving circuit 200, the blood pressure detection circuit 400, and the touch driver 500 may be attached onto the circuit board 300 by a chip on film (COF) method.

Figure 5:
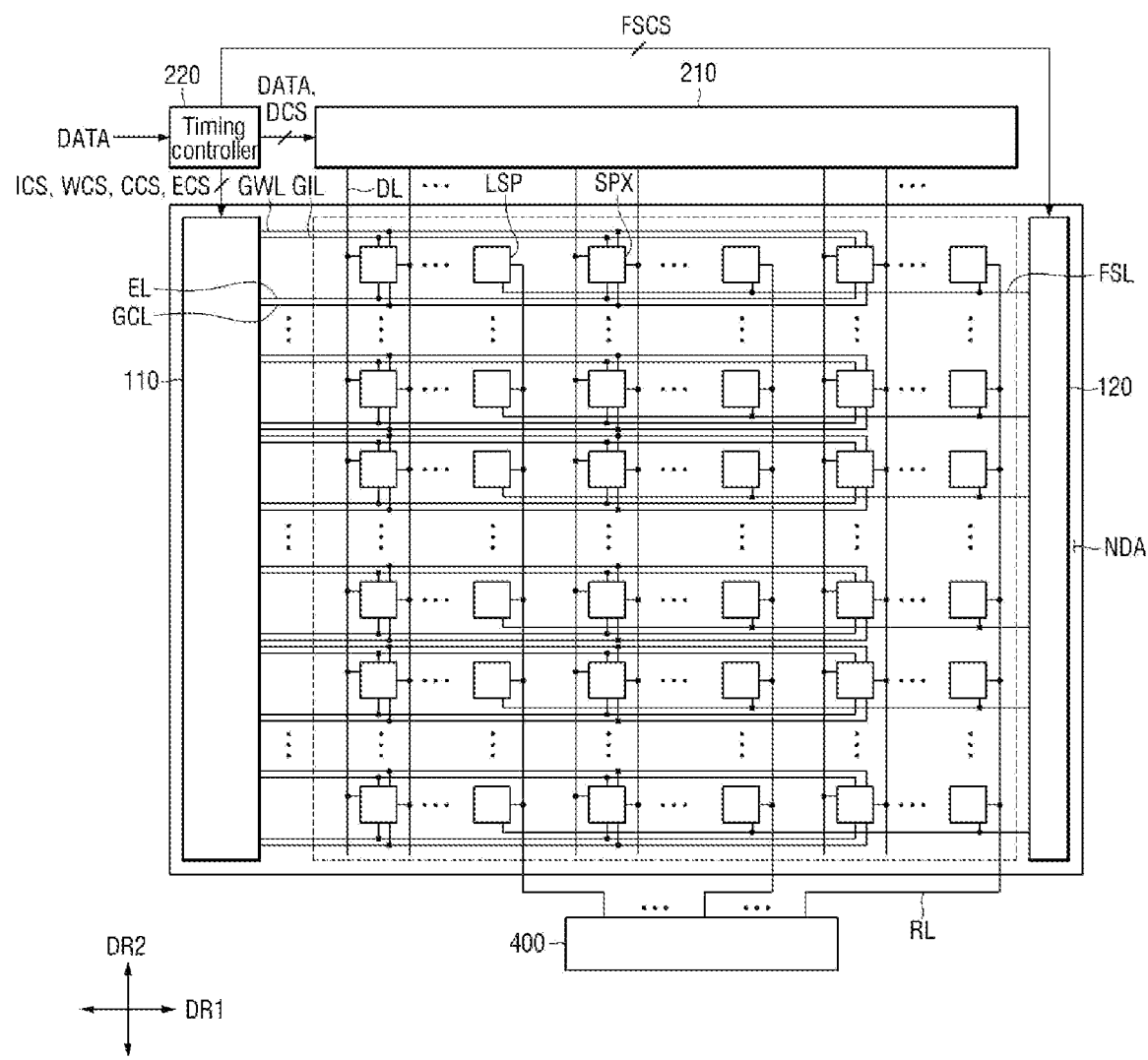
FIG. 5 is a configuration block diagram specifically illustrating a display device according to an embodiment.

FIG. 5 is a configuration block diagram illustrating a display device according to an embodiment.

Referring to FIG. 5, a display device according to an embodiment further includes a display scan driver 110 (e.g., a driver circuit), a light sensing driver 120 (e.g., a driver circuit), a power supply unit (not shown) in addition to the display panel 100, the display driving circuit 200, and the blood pressure detection circuit 400. The display driving circuit 200 may include a data driver 210 and a timing controller 220. In addition, all of the display driving circuit 200, the data driver 210, the display scan driver 110, and the light sensing driver 120 may be integrally formed into a one-chip type.

Referring to FIG. 5, the display panel 100 may include the display pixels SPX, the light sensing pixels LSP, display write lines GWL, display initialization lines GIL, display control lines GCL, light emitting lines EL, data lines DL, light sensing scan lines FSL, and light sensing lines RL which are disposed in the display area DA. Each of the display scan driver 110 and the light sensing driver 120 are disposed in the non-display area NDA.

The display write lines GWL, the display initialization lines GIL, the display control lines GCL, the emission lines EL, and the light sensing scan lines FSL may extend in the first direction DR1. The data lines DL and the light sensing lines RL may extend in the second direction DR2.

The display pixels SPX and the light sensing pixels LSP may be arranged in a matrix form in the first direction DR1 and the second direction DR2 in the display area DA. For example, three display pixels SPX that respectively display red, green, and blue light, and one light sensing pixel LSP may form one unit pixel. The red, green, and blue display pixels SPX and the light sensing pixel LSP constituting each unit pixel may be alternately arranged in a horizontal or vertical stripe form. Each of the red, green, and blue display pixels SPX may be connected to one of the display write lines GWL, one of the display initialization lines GIL, one of the display control lines GCL, and one of the emission lines EL. Each of the display pixels SPX may receive a data voltage of the data line DL according to a display scan signal of the display write line GWL, a display initialization signal of the display initialization line GIL, a display control signal of the display control line GCL, and an emission signal of the emission line EL, and may supply a driving current to the light emitting element according to the data voltage to emit light.

The light sensing pixels LSP may be alternately arranged with the red, green, and blue display pixels SPX in a vertical or horizontal direction. Each of the light sensing pixels LSP is connected to any one of the display write lines GWL, any one of the light sensing scan lines FSL, and any one of the light sensing lines RL. In response to a sensing scan signal from the light sensing scan line FSL, each of the light sensing pixels LSP transmits a light sensing signal according to the amount of reflected light on the front surface to each light sensing line RL.

A display scan driver 110 may be provided in the non-display area NDA. Although the display scan driver 110 is illustrated to be disposed on one side (e.g., left side) of the display panel 100, embodiments of the present disclosure are not limited thereto. For example, the display scan driver 110 may be disposed on both sides (e.g., left and right sides) of the display panel 100. The display scan driver 110 may be electrically connected to the display driving circuit 200 through scan fan-out lines. The display scan driver 110 may receive a write control signal WCS from the display driving circuit 200, generate display scan signals in response to the write control signal WCS, and output the display scan signals to the display write lines GWL.

Specifically, the display scan driver 110 may be connected to the display write lines GWL, the display initialization lines GIL, the display control lines GCL, and the emission lines EL. The display scan driver 110 may include a display signal output unit for outputting display scan signals applied to the display write lines GWL, display initialization signals applied to the display initialization lines GIL, and display control signals applied to the display control lines GCL, and an emission signal output unit for outputting emission signals applied to the emission lines EL.

The display scan driver 110 may receive a write control signal WCS, an initialization control signal ICS, a write control signal CCS, and an emission control signal ECS from the timing controller 220. A display signal output unit of the display scan driver 110 may generate the display scan signals according to the write control signal WCS and output them to the display write lines GWL. In addition, the display signal output unit of the display scan driver 110 may generate the display initialization signals according to the initialization control signal ICS and output them to the display initialization lines GIL. In addition, the display signal output unit of the display scan driver 110 may generate the display control signals according to the write control signal CCS and output them to the display control lines GCL. Further, a emission signal output unit of the display scan driver 110 may generate the emission signals according to the emission control signal ECS and output them to the emission lines EL.

The light sensing driver 120 may be disposed in the non-display area NDA. FIG. 5 illustrates that the light sensing driver 120 is disposed on the other side (e.g., right side) of the display panel 100, but embodiments of the present disclosure are not limited thereto.

The light sensing driver 120 may be electrically connected to the display driving circuit 200 through fan-out lines of the non-display area NDA. The light sensing driver 120 may receive a light sensing control signal FSCS from the display driving circuit 200 and may generate sensing scan signals on at least one horizontal period basis in response to the light sensing control signal FSCS. The light sensing driver 120 sequentially supplies the sensing scan signals to the light sensing scan lines FSL. Accordingly, in response to the sensing scan signals sequentially applied from the light sensing driver 120, the light sensing pixels LSP transmit a light sensing signal according to a light amount detection result to the light sensing lines RL.

In addition, the light sensing driver 120 may sequentially supply reset signals to the light sensing pixels LSP for each horizontal line according to a line selection signal of the light sensing control signal FSCS. In this case, the light sensing driver 120 may sequentially supply the reset signals to the light sensing pixels LSP for each horizontal line according to the line selection signal sequentially inputted on at least one horizontal line basis. Accordingly, each of the light sensing pixels LSP may be reset in response to the reset signal inputted for each horizontal line, and may transmit the light sensing signal according to the light amount detection result to each of the light sensing lines RL in response to the sensing scan signals sequentially applied during a period before the next reset signal is inputted.

The data driver 210 converts digital video data DATA into data voltages and outputs them to the data lines DL. The data driver 210 may output data voltages in synchronization with the display scan signals. Therefore, the display pixels SPX may be selected by the display scan signals of the display scan driver 110, and a data voltage may be supplied to each of the selected display pixels SPX.

The timing controller 220 may receive the timing signals and the digital video data DATA from an external graphic device. For example, the external graphic device may be a graphic card of a computer, a set-top box, or the like, but the embodiment of the present disclosure is not limited thereto.

The timing controller 220 may generate the write control signal WCS, the initialization control signal ICS, the sensing control signal SCS, and the emission control signal ECS to control the operation timing of the display scan driver 110 according to the timing signals. In addition, the timing controller 220 may generate the light sensing control signal FSCS for controlling the reset and scan operation timings of the light sensing driver 120 in response to the timing signals. In addition, the timing controller 220 may generate a data control signal DCS for controlling the operation timing of the data driver 210 according to the timing signals.

The timing controller 220 supplies the write control signal WCS, the initialization control signal ICS, the sensing control signal SCS, and the emission control signal ECS to the display scan driver 110. In addition, the timing controller 220 outputs the light sensing control signal FSCS to the light sensing driver 120. Further, the timing controller 220 outputs the digital video data DATA and the data control signal DCS to the data driver 210.

Meanwhile, the timing controller 220 may receive touch data from the touch driver 500 to determine user's touch coordinates, and then may generate digital video data according to the touch coordinates, or execute an application indicated by an icon displayed on the user's touch coordinates. As another example, the timing controller 220 may receive pressure sensing data from the touch driver 500 to determine pressure sensing coordinates, and then may generate digital video data according to the pressure sensing coordinates or execute an application indicated by an icon displayed on the pressure sensing coordinates. In particular, the timing controller 220 may analyze the pressure sensing data from the pressure sensing unit PSU to detect the user's pressure in real time, and may display the detection result of the user's pressure through a preset pressure display image.

The blood pressure detection circuit 400 receives the light sensing signal inputted through at least one light sensing line RL. In addition, the blood pressure detection circuit 400 may calculate a pulse wave signal reflecting blood changes depending on the heartbeat using the light sensing signal, and measure the user's blood pressure according to the magnitude, the change period, and the like of the pulse wave signal. A blood pressure measurement method of the blood pressure detection circuit 400 will be described in more detail later with reference to the accompanying drawings.

Figure 6:
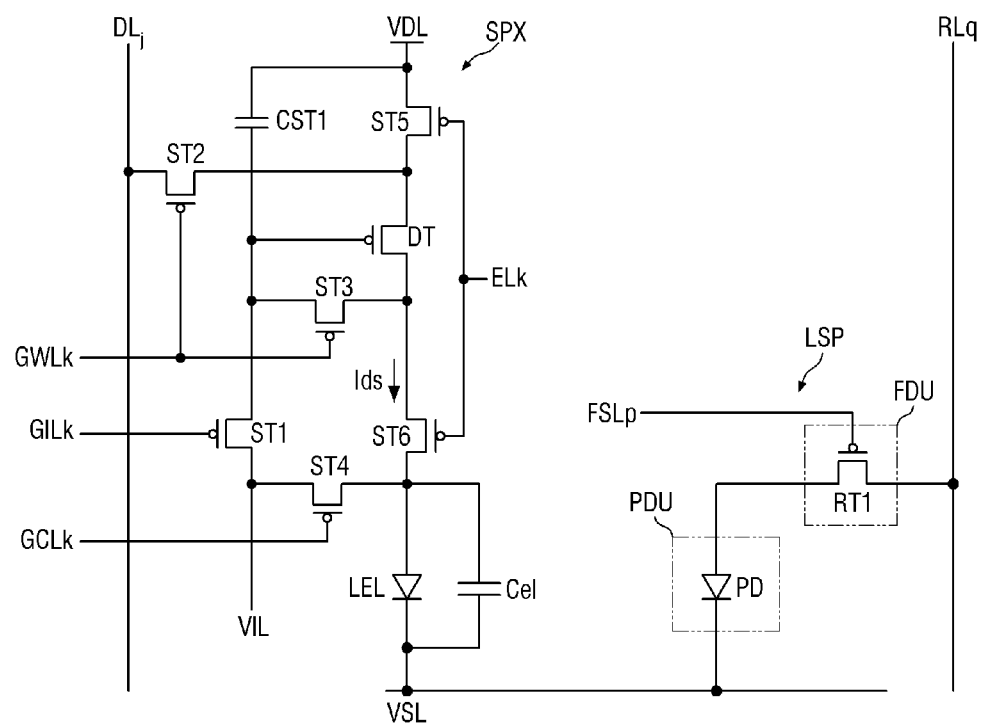
FIG. 6 is a circuit diagram illustrating a display pixel and a light sensing pixel according to an embodiment.

FIG. 6 is a circuit diagram illustrating a display pixel and a light sensing pixel according to an embodiment.

Referring to FIG. 6, the display pixel SPX according to an embodiment is connected to a $k^{th}$ display initialization line GILk, a $k^{th}$ display write line GWLk, and a $k^{th}$ display control line GCLk. In addition, the display pixel SPX may be connected to a first driving voltage line VDL to which the first driving voltage is supplied, a second driving voltage line VSL to which the second driving voltage is supplied, and a third driving voltage line VIL to which the third driving voltage is supplied. Hereinafter, the alphabet letters k, j, i, p, n, m, q, and the like used in place of numbers are defined to be positive integers excluding 0.

The display pixel SPX may include a light emitting portion and a pixel driver. The light emitting portion may include a light emitting element LEL. The pixel driver may include a driving transistor DT, switch elements, and a capacitor CST1. The switch elements include the first to sixth transistors ST1, ST2, ST3, ST4, ST5, and ST6.

The driving transistor DT may include a gate electrode, a first electrode, and a second electrode. The driving transistor DT controls a drain-source current Ids (hereinafter, referred to as "driving current") flowing between the first electrode and the second electrode according to a data voltage applied to the gate electrode. The driving current Ids flowing through a channel of the driving transistor DT is proportional to the square of the difference between a threshold voltage and a voltage Vsg between the first electrode and the gate electrode of the driving transistor DT, as shown in Eq. (1).

$$Ids = k' \times (Vsg - Vth)^2 \quad (1)$$

In Eq. (1), k' is a proportional coefficient determined by the structure and physical characteristics of the driving transistor, Vsg is a voltage between the first electrode and the gate electrode of the driving transistor DT, and Vth is a threshold voltage of the driving transistor DT.

The light emitting element LEL emits light based on the driving current Ids. As the driving current Ids increases, the amount of light emitted from the light emitting element LEL may increase.

The light emitting element LEL may be an organic light emitting diode including an organic light emitting layer disposed between an anode electrode and a cathode electrode. Alternatively, the light emitting element LEL may be an inorganic light emitting element including an inorganic semiconductor disposed between an anode electrode and a cathode electrode. Alternatively, the light emitting element LEL may be a quantum dot light emitting element including a quantum dot light emitting layer disposed between an anode electrode and a cathode electrode. Alternatively, the light emitting element LEL may be a micro light emitting element including a micro light emitting diode disposed between an anode electrode and a cathode electrode.

The anode electrode of the light emitting element LEL may be connected to a first electrode of the fourth transistor ST4 and a second electrode of the sixth transistor ST6, and the cathode electrode of the light emitting element LEL may be connected to the second driving voltage line VSL. A parasitic capacitance Cel may be formed between the anode electrode and the cathode electrode of the light emitting element LEL.

The first transistor ST1 is turned on by the display initialization signal of the $k^{th}$ display initialization line GILk to connect the gate electrode of the driving transistor DT to the third driving voltage line VIL. Accordingly, the third driving voltage VINT of the third driving voltage line VIL may be applied to the gate electrode of the driving transistor DT. The gate electrode of the first transistor ST1 may be connected to the $k^{th}$ display initialization line GILk, the first electrode thereof may be connected to the gate electrode of the driving transistor DT, and the second electrode thereof may be connected to the third driving voltage line VIL.

The second transistor ST2 is turned on by a display scan signal of the $k^{th}$ display write line GWLk to connect the first electrode of the driving transistor DT to a $j^{th}$ data line DLj. Accordingly, the data voltage of the $j^{th}$ data line DLj may be applied to the first electrode of the driving transistor DT. The gate electrode of the second transistor ST2 may be connected to the $k^{th}$ display write line GWLk, the first electrode thereof may be connected to the first electrode of the driving transistor DT, and the second electrode thereof may be connected to the $j^{th}$ data line DLj.

The third transistor ST3 is turned on by the display scan signal of the $k^{th}$ display write line GWLk to connect the gate electrode of the driving transistor DT to the second electrode thereof. When the gate electrode of the driving transistor DT is connected to the second electrode thereof, the driving transistor DT is driven as a diode. The gate electrode of the third transistor ST3 may be connected to the $k^{th}$ display write line GWLk, the first electrode thereof may be connected to the second electrode of the driving transistor DT, and the second electrode thereof may be connected to the gate electrode of the driving transistor DT.

The fourth transistor ST4 is turned on by a display control signal of the $k^{th}$ display control line GCLk to connect the anode electrode of the light emitting element LEL to the third driving voltage line VIL. The third driving voltage of the third driving voltage line VIL may be applied to the anode electrode of the light emitting element LEL. The gate electrode of the fourth transistor ST4 is connected to the $k^{th}$ display control line GCLk, the first electrode thereof is connected to the anode electrode of the light emitting element LEL, and the second electrode thereof is connected to the third driving voltage line VIL.

The fifth transistor ST5 is turned on by an emission signal of a $k^{th}$ emission line ELk to connect the first electrode of the driving transistor DT to the first driving voltage line VDL. The gate electrode of the fifth transistor ST5 is connected to the $k^{th}$ emission line ELk, the first electrode thereof is connected to the first driving voltage line VDL, and the second electrode thereof is connected to the first electrode of the driving transistor DT.

The sixth transistor ST6 is disposed between the second electrode of the driving transistor DT and the anode electrode of the light emitting element LEL. The sixth transistor ST6 is turned on an emission control signal of the $k^{th}$ emission line Elk to connect the second electrode of the driving transistor DT to the anode electrode of the light emitting element LEL. The gate electrode of the sixth transistor ST6 is connected to the $k^{th}$ emission line Elk, the first electrode thereof is connected to the second electrode of the driving transistor DT, and the second electrode thereof is connected to the anode electrode of the light emitting element LEL.

When both the fifth transistor ST5 and the sixth transistor ST6 are turned on, the driving current Ids of the driving transistor DT according to the data voltage applied to the gate electrode of the driving transistor DT may flow to the light emitting element LEL.

The capacitor CST1 is formed between the gate electrode of the driving transistor DT and the first driving voltage line VDL. The first capacitor electrode of the capacitor CST1 may be connected to the gate electrode of the driving transistor DT, and the second capacitor electrode thereof may be connected to the first driving voltage line VDL.

When the first electrode of each of the driving transistor DT and the first to sixth transistors ST1 to ST6 is a source electrode, the second electrode thereof may be a drain electrode. Alternatively, when the first electrode of each of the driving transistor DT and the first to sixth transistors ST1 to ST6 is a drain electrode, the second electrode thereof may be a source electrode.

An active layer of each of the driving transistor DT and the first to sixth transistors ST1 to ST6 may be formed of any one of polysilicon, amorphous silicon, or an oxide semiconductor. In FIG. 6, the first to sixth transistors ST1 to ST6, and the driving transistor DT have been mainly described as being formed of a P-type MOSFET, but embodiments of the present disclosure is not limited thereto. For example, the first to sixth transistors ST1 to ST6, and the driving transistor DT may be formed of an N-type MOSFET. Alternatively, at least one of the first to sixth transistors ST1 to ST6 may be formed of an N-type MOSFET.

The light sensing pixel LSP according to an embodiment is connected to a $p^{th}$ light sensing scan line FSLp and a $q^{th}$ light sensing line RLq.

The light sensing pixel LSP may include a light sensing portion PDU and a sensing driver FDU. The light sensing portion PDU may include a light sensing element PD. The sensing driver FDU may include a sensing signal transistor SRT.

The voltage of a sensing anode electrode of the light sensing element PD may vary depending on light incident on the light sensing element PD. For example, as the amount of light incident on the light sensing element PD increases, the voltage of the sensing anode electrode of the light sensing element PD may increase.

The light sensing element PD may be a photodiode including an anode electrode, a PIN semiconductor layer, and a cathode electrode. The sensing anode electrode of the light sensing element PD may be connected to the first electrode of the sensing signal transistor SRT, and the cathode electrode thereof may be connected to the second driving voltage line VSL. The PIN semiconductor layer of the light sensing element PD may include a P-type semiconductor layer connected to the anode electrode, an N-type semiconductor layer connected to the cathode electrode, and an I-type semiconductor layer disposed between the P-type semiconductor layer and the N-type semiconductor layer. In this case, the I-type semiconductor layer is depleted by the P-type semiconductor layer PL and the N-type semiconductor layer NL to generate an electric field therein, and holes and electrons generated by light drift by the electric field. Due to this, the holes may be collected to the anode electrode through the P-type semiconductor layer and the electrons may be collected to the cathode electrode through the N-type semiconductor layer.

The sensing signal transistor SRT is turned on by the sensing scan signal of the $p^{th}$ light sensing scan line FSLp to connect the sensing anode electrode of the light sensing element PD to the $q^{th}$ light sensing line RLq. Accordingly, the voltage of the sensing anode electrode of the light sensing element PD may be applied to the $q^{th}$ light sensing line RLq. The gate electrode of the sensing signal transistor SRT may be connected to the $p^{th}$ light sensing scan line FSLp, the first electrode thereof may be connected to the sensing anode electrode of the light sensing element PD, and the second electrode thereof may be connected to the $q^{th}$ light sensing line RLq.

Figure 7:
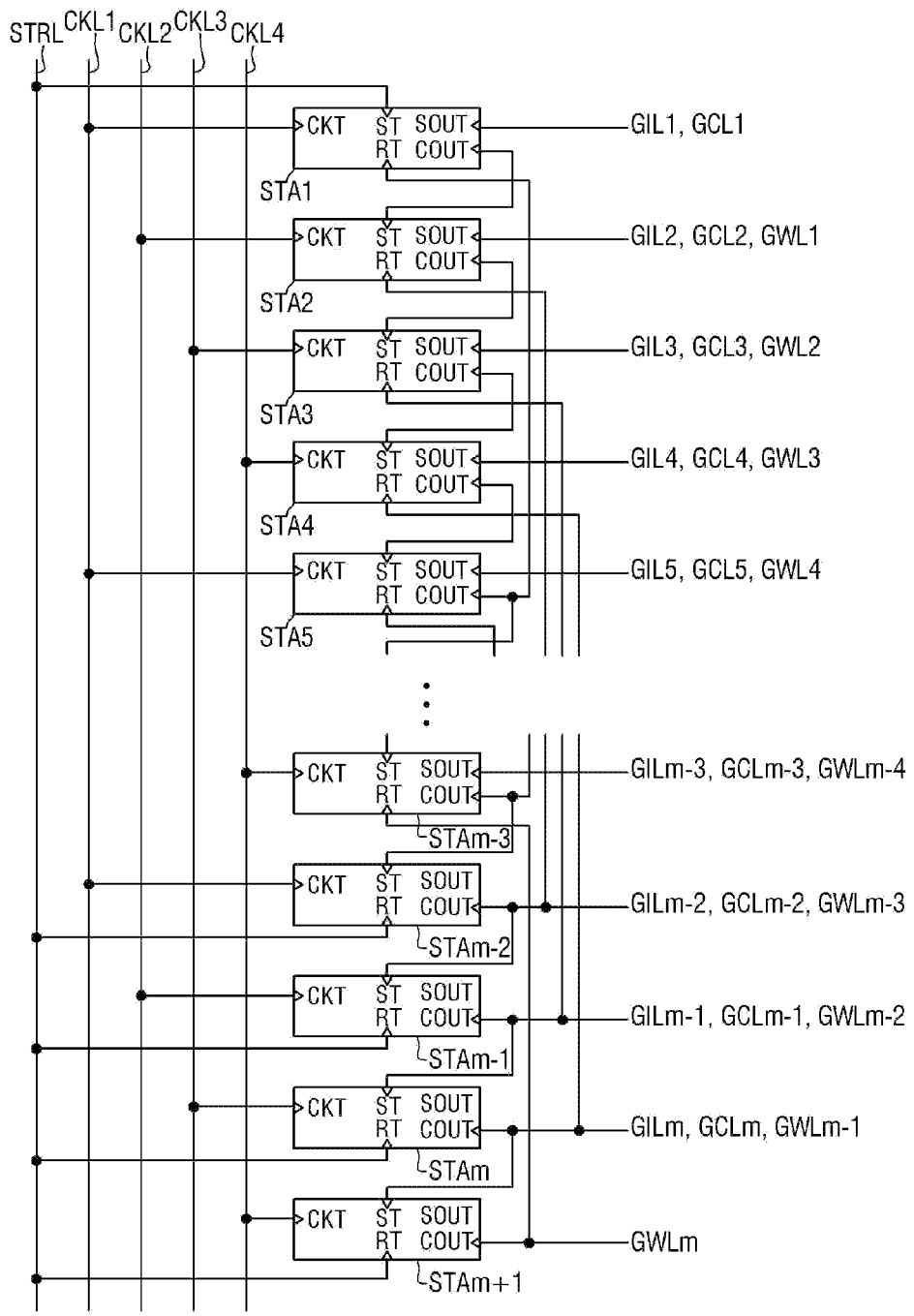
FIG. 7 is a diagram illustrating a display scan driver according to an embodiment.

FIG. 7 is a diagram illustrating a display scan driver according to an embodiment. Referring to FIG. 7, the display scan driver 110 may include a plurality of display stages STA1, STA2, STA3, STA4, . . . , STAm−1, STAm, and STAm+1 (m being a positive integer). Each of the plurality of display stages STA1 to STAm+1 may include a start signal input terminal ST, a reset signal input terminal RT, a clock signal input terminal CKT, a display signal output terminal SOUT, and a carry signal output terminal COUT.

The start signal input terminal ST of each of the plurality of display stages STA1 to STAm+1 may be connected to a start line STRL or the carry signal output terminal COUT of a previous display stage. For example, the start signal input terminal ST of a first display stage STA1 may be connected to the start line STRL to which a display start signal is inputted. In addition, the start signal input terminal ST of each of the plurality of display stages STA2 to STAm+1 excluding the first display stage STA1 may be connected to the carry signal output terminal COUT of a previous display stage. For example, the start signal input terminal ST of a second display stage STA2 may be connected to the carry signal output terminal COUT of the first display stage STA1, and the start signal input terminal ST of a third display stage STA3 may be connected to the carry signal output terminal COUT of the second display stage STA2.

The reset signal input terminal RT of each of the plurality of display stages STA1 to STAm+1 may be connected to the carry signal output terminal COUT of a subsequent display stage. For example, the reset signal input terminal RT of the first display stage STA1 may be connected to the carry signal output terminal COUT of a fifth display stage STA5.

The clock signal input terminal CKT of each of the plurality of display stages STA1 to STAm+1 may be connected to one of clock lines CKL1, CKL2, CKL3, and CKL4.

The plurality of display stages STA1 to STAm+1 may be alternately connected to the clock lines CKL1 to CKL4. For example, the clock signal input terminal CKT of the first display stage STA1 may be connected to a first clock line CKL1, and the clock signal input terminal CKT of the second display stage STA2 may be connected to a second clock line CKL2. The clock signal input terminal CKT of the third display stage STA3 may be connected to a third clock line CKL3, and the clock signal input terminal CKT of a fourth display stage STA4 may be connected to a fourth clock line CKL4.

The scan signal output terminal SOUT of each of the plurality of display stages STA1 to STAm+1 may be connected to the display write line, the display initialization line, and the display control line corresponding thereto. For example, the first display stage STA1 may be connected to a first display initialization line GIL1 and a first display control line GCL1. In addition, the second display stage STA2 may be connected to a second display initialization line GIL2, a second display control line GCL2, and a first display write line GWL1. In addition, the third display stage STA3 may be connected to a third display initialization line GIL3, a third display control line GCL3, and a second display write line GWL2. In addition, the fourth display stage STA4 may be connected to a fourth display initialization line GIL4, a fourth display control line GCL4, and a third display write line GWL3. In addition, an $(m-1)^{th}$ display stage STAm−1 may be connected to an $(m-1)^{th}$ display initialization line GILm-1, an (m-1)$^{th}$ display control line GCLm-1, and an (m-2)$^{th}$ display write line GWLm-2. In addition, an m$^{th}$ display stage STAm may be connected to an m$^{th}$ display initialization line GILm, an m$^{th}$ display control line GCLm, and an (m-1)$^{th}$ display write line GWLm-1. Further, an (m+1)$^{th}$ display stage STAm+1 may be connected to an m$^{th}$ display write line GWLm.

The carry signal output terminal COUT of each of the plurality of display stages STA1 to STAm+1 may be connected to the reset signal input terminal RT of a previous display stage and the start signal input terminal ST of a subsequent display stage. However, the carry signal output terminal COUT of each of the first display stage STA1, the second display stage STA2, the third display stage STA3, and the fourth display stage STA4 may be connected only to the start signal input terminal ST of a subsequent display stage.

Figure 8:
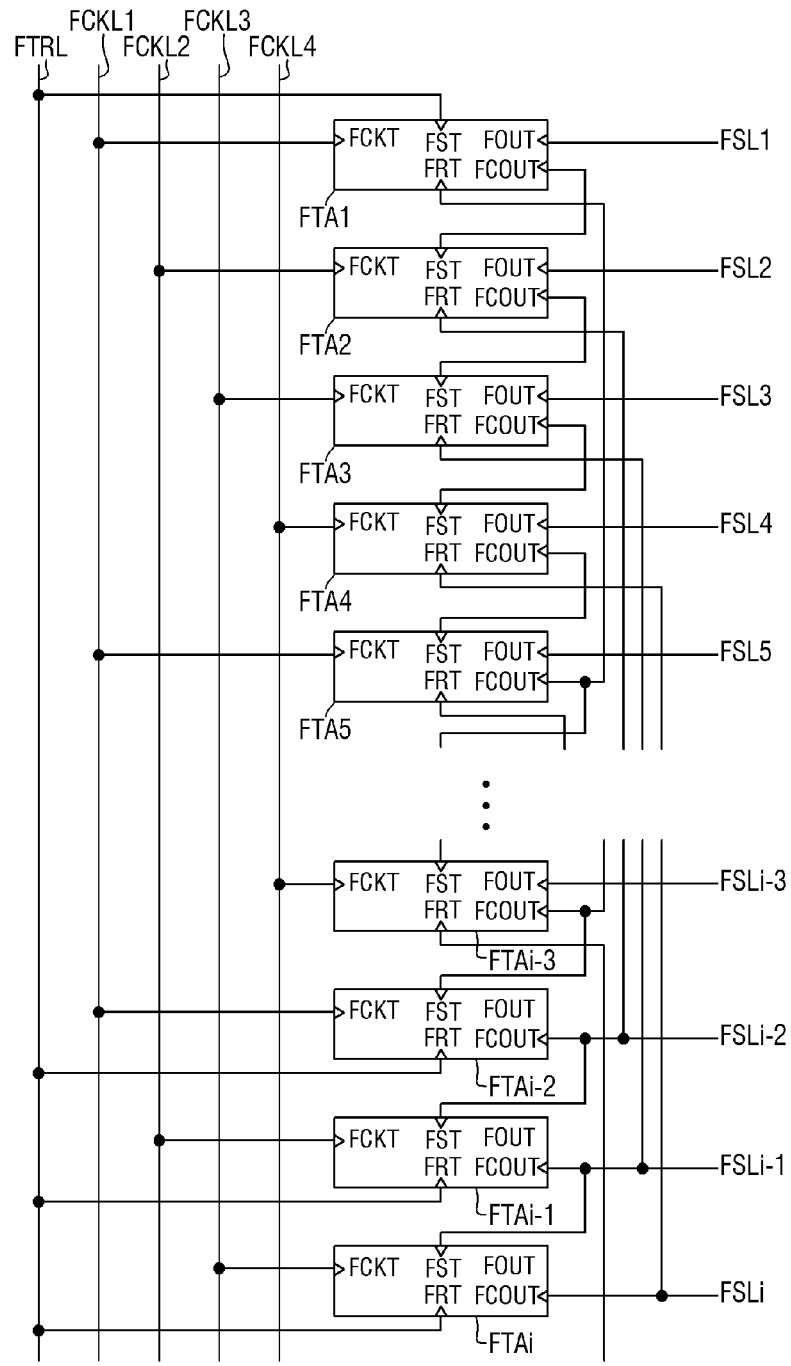
FIG. 8 is a diagram illustrating a light sensing driver according to an embodiment.

FIG. 8 is a diagram illustrating a light sensing driver according to one embodiment.

Referring to FIG. 8, the light sensing driver 120 may include a plurality of sensing stages FTA1, FTA2, FTA3, FTA4, . . . , FTAi-1, and FTAi (i being an integer less than m). Each of the plurality of sensing stages FTA1 to FTAi may include a sensing start signal input terminal FST, a sensing reset signal input terminal FRT, a sensing clock signal input terminal FCKT, a sensing scan signal output terminal FOUT, and a sensing carry signal output terminal FCOUT.

The sensing start signal input terminal FST of each of the plurality of sensing stages FTA1 to FTAi may be connected to a sensing start line FTRL or the sensing carry signal output terminal FCOUT of a previous sensing stage. For example, the sensing start signal input terminal FST of a first sensing stage FTA1 may be connected to the sensing start line FTRL to which a sensing start signal is inputted. In addition, the sensing start signal input terminal FST of each of the plurality of sensing stages FTA2 to FTAi excluding the first sensing stage FTA1 may be connected to the sensing carry signal output terminal FCOUT of a previous sensing stage. For example, the sensing start signal input terminal FST of a second sensing stage FTA2 may be connected to the sensing carry signal output terminal FCOUT of the first sensing stage FTA1, and the sensing start signal input terminal FST of a third sensing stage FTA3 may be connected to the sensing carry signal output terminal FCOUT of the second sensing stage FTA2.

The sensing reset signal input terminal FRT of each of the plurality of sensing stages FTA1 to FTAi may be connected to the sensing carry signal output terminal FCOUT of a subsequent sensing stage. For example, the sensing reset signal input terminal FRT of the first sensing stage FTA1 may be connected to the sensing carry signal output terminal FCOUT of a fifth sensing stage FTA5.

The sensing clock signal input terminal FCKT of each of the plurality of sensing stages FTA1 to FTAi may be connected to one of sensing clock lines FCKL1, FCKL2, FCKL3, and FCKL4.

The plurality of sensing stages FTA1 to FTAi may be alternately connected to the sensing clock lines FCKL1 to FCKL4. For example, the sensing clock signal input terminal FCKT of the first sensing stage FTA1 may be connected to a first sensing clock line FCKL1, and the sensing clock signal input terminal FCKT of the second sensing stage FTA2 may be connected to a second sensing clock line FCKL2. The sensing clock signal input terminal FCKT of the third sensing stage FTA3 may be connected to a third sensing clock line FCKL3, and the sensing clock signal input terminal FCKT of a fourth sensing stage FTA4 may be connected to a fourth sensing clock line FCKL4.

The plurality of sensing stages FTA1, FTA2, FTA3, FTA4, . . . , FTAi-1, and FTAi may be connected to light sensing scan lines FSL1, FSL2, FSL3, FSL4, . . . , FSLi-1, and FSLi. The display scan signal output terminal FOUT of each of the plurality of sensing stages FTA1 to FTAi may be connected to the light sensing scan line corresponding thereto. For example, the first sensing stage FTA1 may be connected to a first light sensing scan line FSL1, and the second sensing stage FTA2 may be connected to a second light sensing scan line FSL2. In addition, the third sensing stage FTA3 may be connected to a third light sensing scan line FSL3, and the fourth sensing stage FTA4 may be connected to a fourth light sensing scan line FSL4. In addition, an (i-1)$^{th}$ sensing stage FTAi-1 may be connected to an (i-1)$^{th}$ light sensing scan line FSLi-1, and an i$^{th}$ sensing stage FTAi may be connected to an i$^{th}$ light sensing scan line FSLi.

The sensing carry signal output terminal FCOUT of each of the plurality of sensing stages FTA1 to FTAi may be connected to the sensing reset signal input terminal FRT of a previous sensing stage and the sensing start signal input terminal FST of a subsequent sensing stage. However, the sensing carry signal output terminal FCOUT of each of the first sensing stage FTA1, the second sensing stage FTA2, the third sensing stage FTA3, and the fourth sensing stage FTA4 may be connected only to the sensing start signal input terminal FST of a subsequent sensing stage.

Meanwhile, the plurality of display stages STA1 to STAm+1 provide the display scan signals, the display initialization signals, and the display control signals to the display pixels SPX of the display area DA. The plurality of sensing stages FTA1 to FTAi provide the sensing scan signals (and reset signals) to the sensing drivers FDU connected to the light sensing portions PDU of the display area DA. The number of the light sensing scan lines FSL may be the same as the number of the display write lines GWL. Therefore, the number of the plurality of sensing stages FTA1 to FTAi may be the same as the number of the plurality of display stages STA1 to STAm+1.

Figure 9:
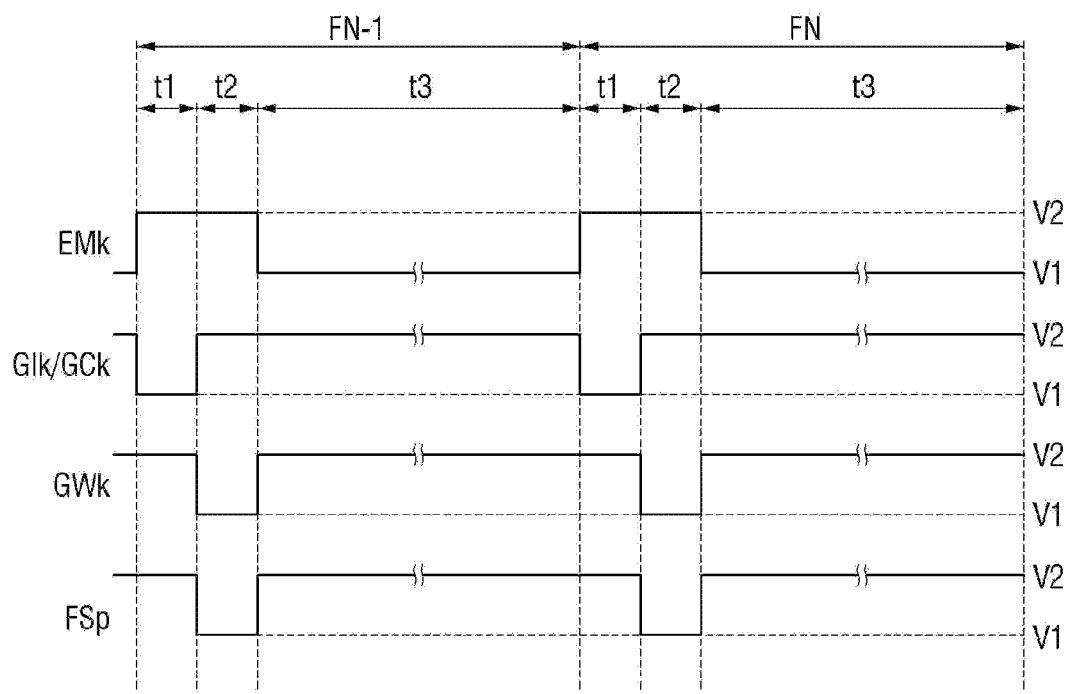
FIG. 9 is a waveform diagram illustrating scan signals inputted to a light sensing pixel and a display pixel according to an embodiment.

FIG. 9 is a waveform diagram illustrating scan signals inputted to a light sensing pixel and a display pixel according to an embodiment.

FIG. 9 shows a k$^{th}$ display emission signal EMk applied to the k$^{th}$ emission line ELk, a k$^{th}$ display initialization signal GIk applied to the k$^{th}$ display initialization line GILk, a k$^{th}$ display control signal GCk applied to the k$^{th}$ display control line GCLk, a k$^{th}$ display scan signal GWk applied to the k$^{th}$ display write line GWLk, and a p$^{th}$ sensing scan signal FSp applied to the p$^{th}$ light sensing scan line FSLp, during an (N-1)$^{th}$ frame period FN-1 and an N$^{th}$ frame period FN.

The k$^{th}$ display initialization signal GIk controls turning on/off of the first transistor ST1 of the display pixel SPX. The k$^{th}$ display control signal GCk controls turning on/off of the fourth transistor ST4 of the display pixel SPX. The k$^{th}$ display scan signal GWk controls turning on/off of the second transistor ST2 and the third transistor ST3. The k$^{th}$ display emission signal EMk controls turning on/off of the fifth transistor ST5 and the sixth transistor ST6. The p$^{th}$ sensing scan signal FSp is a signal for controlling turning on/off of the sensing signal transistor SRT.

Each of the (N-1)$^{th}$ frame period FN-1 and the N$^{th}$ frame period FN may include a first period t1, a second period t2, and a third period t3. The first period t1 is a period during which the gate electrode of the driving transistor DT is initialized to the third driving voltage VINT. The second period t2 is a period during which a data voltage is supplied to the gate electrode of the driving transistor DT and a threshold voltage of the driving transistor DT is sampled. The third period t3 is a period during which the light emitting element LEL emits light according to the gate voltage of the driving transistor DT. In addition, the first period t1 and the third period t3 are periods during which the light sensing element PD is exposed to light, and the second period t2 is a period during which the anode voltage of the light sensing element PD is detected.

The $k^{th}$ display emission signal EMk has a first level voltage V1 during the third period t3 and a second level voltage V2 during the first period t1 and the second period t2. The $k^{th}$ display scan signal GWk has the first level voltage V1 during the second period t2 and the second level voltage V2 during the first period t1 and the third period t3.

The $k^{th}$ display initialization signal GIk and the $k^{th}$ display control signal GCk have the first level voltage V1 during the first period t1, and the second level voltage V2 during the second period t2 and the third period t3. That is, the $k^{th}$ display initialization signal GIk and the $k^{th}$ display control signal GCk may be substantially the same.

The $p^{th}$ sensing scan signal FSp has the first level voltage V1 during the first period t1 and the second level voltage V2 during the second period t2 and the third period t3. The $p^{th}$ sensing scan signal FSp may be substantially the same as the $k^{th}$ display scan signal GWk.

In an embodiment, each of the first period t1 and the second period t2 is one horizontal period. One horizontal period indicates a period during which a data voltage is supplied to each of the display pixels SPX disposed in one horizontal line (or one pixel row) of the display panel 100, and thus may be defined as one horizontal line scan period. The display pixels SPX arranged in one horizontal line may be defined as sub-pixels connected to one display initialization line, one display write line, one display control line, and one emission line.

The first level voltage V1 may be a turn-on voltage capable of turning on the first to sixth transistors ST1 to ST6 and the sensing signal transistor SRT. The second level voltage V2 may be a turn-off voltage capable of turning off the first to sixth transistors ST1 to ST6 and the sensing signal transistor SRT. The second level voltage V2 may have a level higher than that of the first level voltage V1.

Hereinafter, the operation of the display pixel SPX during the first period t1, the second period t2, and the third period t3 will be described with reference to FIGS. 6 and 9.

Firstly, in the first period t1, the $k^{th}$ display initialization signal GIk having the first level voltage V1 is supplied to the $k^{th}$ display initialization line GILk, and the $k^{th}$ display control signal GCk having the first level voltage V1 is supplied to the $k^{th}$ display control line GCLk.

During the first period t1, the first transistor ST1 is turned on by the $k^{th}$ display initialization signal GIk having the first level voltage V1. Due to the turn-on of the first transistor ST1, the third driving voltage VINT of the third driving voltage line VIL is applied to the gate electrode of the driving transistor DT. When the initialization voltage VINT is applied to the gate electrode of the driving transistor DT during the first period t1, the voltage Vsg between the first electrode and the gate electrode of the driving transistor DT is greater than the threshold voltage Vth of the driving transistor DT, so that the driving transistor DT may be turned on. That is, since an on bias may be applied to the driving transistor DT, the hysteresis characteristic of the driving transistor DT may be improved.

In addition, during the first period t1, the fourth transistor ST4 is turned on by the $k^{th}$ display control signal GCk having the first level voltage V1. Therefore, due to the turn-on of the fourth transistor ST4 during the first period t1, the anode electrode of the light emitting element LEL may be initialized to the third driving voltage VINT of the third driving voltage line VIL.

Secondly, during the second period t2, the $k^{th}$ display scan signal GWk having the first level voltage V1 is supplied to the $k^{th}$ display write line GWLk. Therefore, during the second period t2, each of the second transistor ST2 and the third transistor ST3 is turned on by the $k^{th}$ display scan signal GWk having the first level voltage V1.

Due to the turn-on of the third transistor ST3 during the second period t2, the gate electrode and the second electrode of the driving transistor DT are connected to each other, and the driving transistor DT is driven as a diode. In addition, due to the turn-on of the second transistor ST2 during the second period t2, a data voltage Vdata is supplied to the first electrode of the driving transistor DT. In this case, since the voltage Vsg (=Vdata−VINT) between the first electrode and the gate electrode of the driving transistor DT is less than the threshold voltage Vth, the driving transistor DT forms a current path until the voltage Vsg between the first electrode and the gate electrode reaches the threshold voltage Vth. For this reason, during the second period t2, the gate electrode and the second electrode of the driving transistor DT rise to a difference voltage Vdata−Vth between the data voltage Vdata and the threshold voltage Vth of the driving transistor DT.

Thirdly, the $k^{th}$ emission signal EMk having the first level voltage V1 is supplied to the $k^{th}$ emission line ELk during the third period t3. During the third period t3, each of the fifth transistor ST5 and the sixth transistor ST6 is turned on by the $k^{th}$ emission signal EMk having the first level voltage V1.

Due to the turn-on of the fifth transistor ST5, the first electrode of the driving transistor DT is connected to the first driving voltage line VDL. Due to the turn-on of the sixth transistor ST6, the second electrode of the driving transistor DT is connected to the anode electrode of the light emitting element LEL.

When the fifth transistor ST5 and the sixth transistor ST6 are turned on, the driving current Ids flowing according to the voltage of the gate electrode of the driving transistor DT may be supplied to the light emitting element LEL. The driving current Ids may be defined as in Eq. (2).

$$Ids = k' \times \{VDD-(V\text{data}-Vth)-Vth\}^2 \quad (2)$$

In Eq. (2), k' is a proportional coefficient determined by the structure and physical characteristics of the driving transistor DT, Vth is the threshold voltage of the driving transistor DT, VDD is the first driving voltage of the first driving voltage line VDL, and Vdata is the data voltage. The voltage of the gate electrode of the driving transistor DT is Vdata−Vth, and the voltage of the first electrode thereof is VDD. When Eq. (2) is summarized, Eq. (3) is derived.

$$Ids = k' \times (VDD - V\text{data})^2 \quad (3)$$

Consequently, as illustrated in Eq. (3), the driving current Ids does not depend on the threshold voltage Vth of the driving transistor DT. That is, the threshold voltage Vth of the driving transistor DT may be compensated.

Hereinafter, the operation of the light sensing pixel LSP during the first period t1, the second period t2, and the third period t3 will be described with reference to FIGS. 6 and 9.

Firstly, the $p^{th}$ sensing scan signal FSp having the second level voltage V2 is supplied to the $p^{th}$ sensing scan line FSLp during the first period t1. Therefore, the sensing signal transistor SRT may be turned off during the first period t1 and the third period t3. Accordingly, the voltage of the sensing anode electrode of the light sensing element PD may increase according to light incident during the first period t1 and the third period t3. For example, as the amount of light incident on the light sensing element PD increases, the voltage of the sensing anode electrode of the light sensing element PD may increase.

Secondly, the $p^{th}$ sensing scan signal FSp having the first level voltage V1 is supplied to the $p^{th}$ sensing scan line FSLp during the second period t2. The sensing signal transistor SRT is turned on by the $p^{th}$ sensing scan signal FSp having the first level voltage V1. Due to the turn-on of the sensing signal transistor SRT, the sensing anode electrode of the light sensing element PD may be connected to the $q^{th}$ light sensing line RLq. Therefore, the blood pressure detection circuit 400 may sense the voltage of the sensing anode electrode of the light sensing element PD through the $q^{th}$ light sensing line RLq.

As shown in FIG. 9, the $k^{th}$ display scan signal GWk and the $p^{th}$ sensing scan signal FSp may be substantially the same. To this end, the plurality of sensing stages FTA1 to FTAi shown in FIG. 8 may be driven at substantially the same timing as some of the plurality of display stages STA1 to STAm+1 shown in FIG. 7. That is, the plurality of sensing stages FTA1 to FTAi may be driven at substantially the same timing as $r^{th}$ (r being an integer less than m) to $s^{th}$ (s being an integer greater than r and less than or equal to m) display stages of the plurality of display stages STA1 to STAm+1.

In addition, a sensing start signal inputted to the sensing start signal input terminal FST of the first sensing stage FTA1 may be substantially the same as a carry signal of a previous stage inputted to the start signal input terminal ST of the $r^{th}$ display stage. In addition, sensing clock signals applied to the sensing clock lines FCKL1, FCKL2, FCKL3 and FCKL4 may be substantially the same as display clock signals applied to the display clock lines CKL1, CKL2, CKL3 and CKL4.

Figure 10:
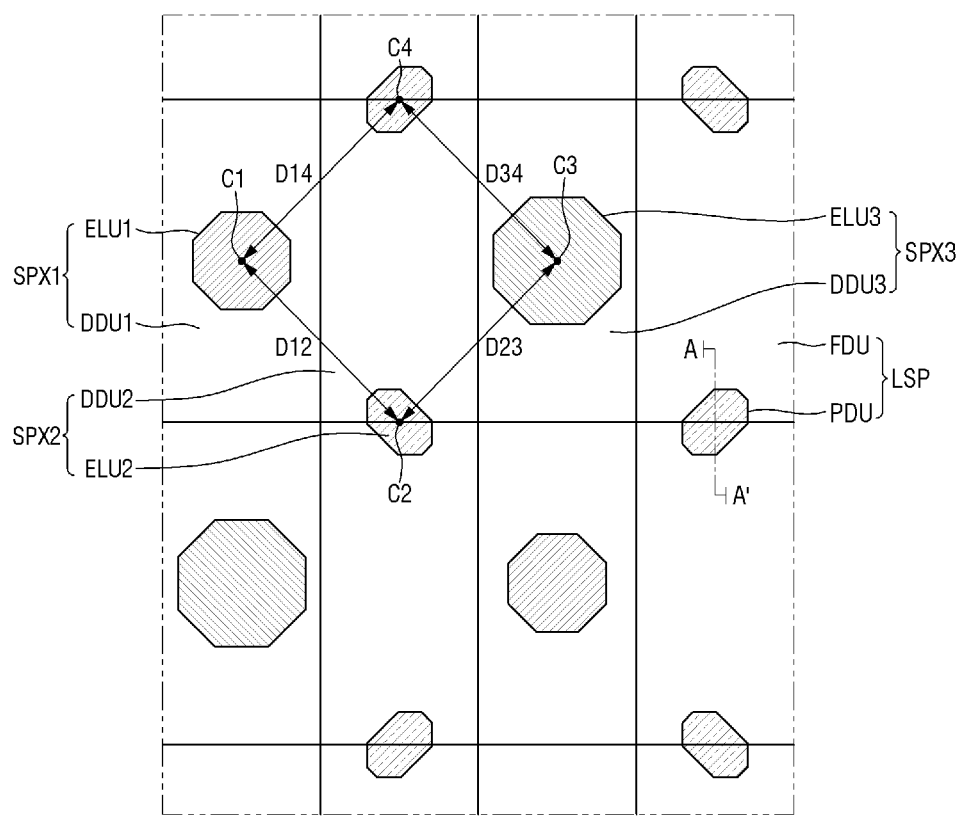
FIG. 10 is a layout diagram illustrating a display area according to an embodiment.

FIG. 10 is a layout diagram illustrating a display area according to an embodiment.

Referring to FIG. 10, the display area DA may include first display pixels SPX1, second display pixels SPX2, third display pixels SPX3, and light sensing pixels LSP. The display pixels SPX may be divided into the first display pixels SPX1, the second display pixels SPX2, and the third display pixels SPX3. The light sensing pixels LSP as well as the first display pixel SPX1, the second display pixel SPX2, and the third display pixel SPX3 may be defined as a unit display pixel USPX. The unit display pixel USPX may be defined as the smallest unit of display pixels capable of sensing light while displaying white.

The first display pixel SPX1 may include a first light emitting portion ELU1 that emits first light, and a first pixel driver DDU1 for applying a driving current to the light emitting element of the first light emitting portion ELU1. The first light may be light of a red wavelength band. For example, the main peak wavelength of the first light may be located at approximately 600 nm to 750 nm.

The second display pixel SPX2 may include a second light emitting portion ELU2 that emits second light, and a second pixel driver DDU2 for applying a driving current to the light emitting element of the second light emitting portion ELU2. The second light may be light of a green wavelength band. For example, the main peak wavelength of the second light may be located at approximately 480 nm to 560 nm.

The third display pixel SPX3 may include a third light emitting portion ELU3 that emits third light, and a third pixel driver DDU3 for applying a driving current to the light emitting element of the third light emitting portion ELU3. The third light may be light of a blue wavelength band. For example, the main peak wavelength of the third light may be located at approximately 370 nm to 460 nm.

The light sensing pixel LSP includes the light sensing portion PDU and the sensing driver FDU.

In the unit display pixel USPX, the first pixel driver DDU1 and the second pixel driver DDU2 may be disposed in the first direction DR1, and the third pixel driver DDU3 and the sensing driver FDU may be disposed in the first direction DR1. In the unit display pixel USPX, the first pixel driver DDU1 and the third pixel driver DDU3 may be disposed in the second direction DR2, and the second pixel driver DDU2 and the sensing driver FDU may be disposed in the second direction DR2.

The first light emitting portion ELU1 may overlap the first pixel driver DDU1, and the third light emitting portion ELU3 may overlap the third pixel driver DDU3. Each of the second light emitting portion ELU2 and the light sensing portion PDU may overlap the second pixel driver DDU2 and the sensing driver FDU. Each of the second light emitting portion ELU2 and the light sensing portion PDU may be disposed at a boundary between the second pixel driver DDU2 and the sensing driver FDU.

The first light emitting portion ELU1, the second light emitting portion ELU2, the third light emitting portion ELU3, and the light sensing portion PDU may have an octagonal shape in plan view, but are not limited thereto. The first light emitting portion ELU1, the second light emitting portion ELU2, the third light emitting portion ELU3, and the light sensing portion PDU may have a quadrangular shape such as a rhombus, or another polygonal shape other than a quadrangle and an octagon in plan view.

Due to the arrangement position and planar shape of the first light emitting portion ELU1, the second light emitting portion ELU2, the third light emitting portion ELU3, and the light sensing portion PDU, a distance D12 between a center C1 of the first light emitting portion ELU1 and a center C2 of the second light emitting portion ELU2 adjacent to each other, a distance D23 between the center C2 of the second light emitting portion ELU2 and a center C3 of the third light emitting portion ELU3 adjacent to each other, a distance D14 between the center C1 of the first light emitting portion ELU1 and a center C4 of the light sensing portion PDU, and a distance D34 between the center C3 of the third light emitting portion ELU3 and the center C4 of the light sensing portion PDU may be substantially the same.

Figure 11:
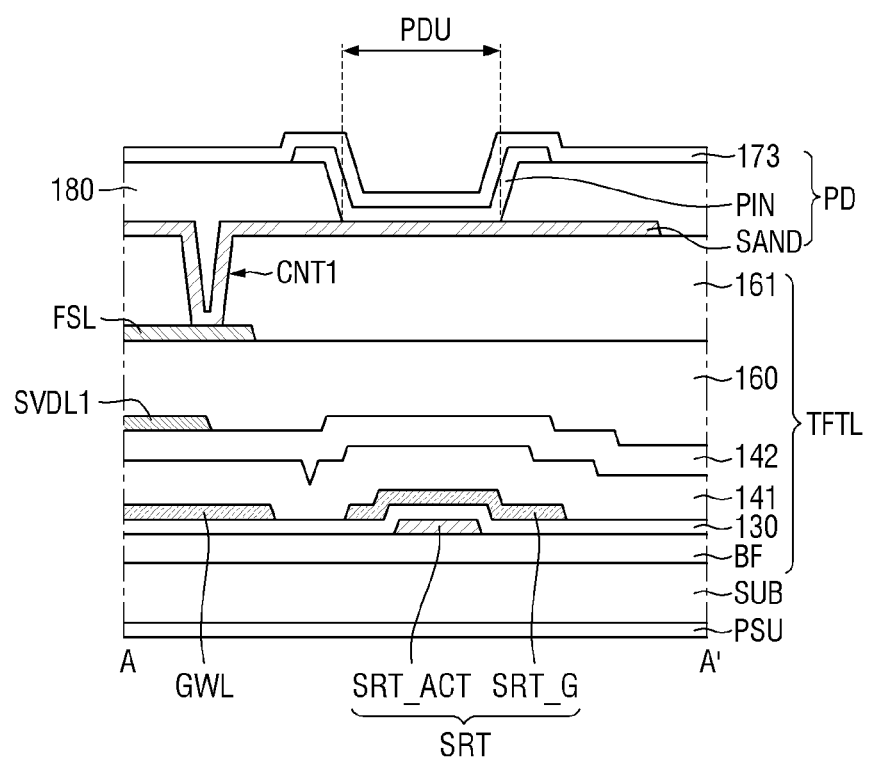
FIG. 11 is a cross-sectional view of a display panel taken along line A-A' of FIG. 10.

FIG. 11 is a cross-sectional view of a display panel taken along line A-A' of FIG. 10. Specifically, FIG. 11 is a cross-sectional view showing a part of a cross section of the light sensing portion PDU and the sensing driver FDU.

Referring to FIG. 11, a thin film transistor layer TFTL including the sensing signal transistor SRT may be formed on the substrate SUB, and the light sensing element PD may be formed on the thin film transistor layer TFTL. The pressure sensing unit PSU may be disposed on the rear surface of the substrate SUB.

The thin film transistor layer TFTL on the front surface of the substrate SUB includes the sensing signal transistor SRT, a gate insulating layer 130, a first interlayer insulating layer 141, a second interlayer insulating layer 142, a first organic layer 160, and a second organic layer 161.

In an embodiment, a buffer layer BF is formed on one surface of the substrate SUB. The buffer layer BF may be formed on one surface of the substrate SUB to protect the sensing signal transistor SRT from moisture penetrating through the substrate SUB susceptible to moisture permeation. The buffer layer BF may be formed of a plurality of inorganic layers that are alternately stacked. For example, the buffer layer BF may be formed of multiple layers in which one or more inorganic layers of a silicon nitride layer, a silicon oxynitride layer, a silicon oxide layer, a titanium oxide layer and an aluminum oxide layer are alternately stacked.

An active layer SRT_ACT may be formed on the buffer layer BF, as a channel region of the sensing signal transistor SRT. The active layer SRT_ACT may include polycrystalline silicon, monocrystalline silicon, low-temperature polycrystalline silicon, amorphous silicon, or an oxide semiconductor. The gate insulating layer 130 may be formed on the active layer SRT_ACT. The gate insulating layer 130 may be formed of an inorganic layer, for example, a silicon nitride layer, a silicon oxynitride layer, a silicon oxide layer, a titanium oxide layer, or an aluminum oxide layer.

A gate layer SRT_G of the sensing signal transistor SRT, the display write line GWL, and the like may be formed on the gate insulating layer 130. The gate layer SRT_G of the sensing signal transistor SRT and the display write line GWL may be formed of a single layer or multiple layers made of any one of molybdenum (Mo), aluminum (Al), chromium (Cr), gold (Au), titanium (Ti), nickel (Ni), neodymium (Nd), and copper (Cu), or an alloy thereof.

A first interlayer insulating layer 141 may be formed on the gate insulating layer 130 and the sensing signal transistor SRT. The first interlayer insulating layer 141 may be formed of an inorganic layer, for example, a silicon nitride layer, a silicon oxynitride layer, a silicon oxide layer, a titanium oxide layer, or an aluminum oxide layer. The first interlayer insulating layer 141 may include a plurality of inorganic layers.

Wires such as the display initialization line GIL and the display control line GCL may be formed on the first interlayer insulating layer 141. In addition, the second interlayer insulating layer 142 may be further formed on the first interlayer insulating layer 141 and the wires.

The display control line GCL, the display initialization line GIL, or the like may be further formed on the second interlayer insulating layer 142, as a single layer or multiple layers made of any one of molybdenum (Mo), aluminum (Al), chromium (Cr), gold (Au), titanium (Ti), nickel (Ni), neodymium (Nd), and copper (Cu), or an alloy thereof.

A first organic layer 160 may be formed on the second interlayer insulating layer 142 to flatten a stepped portion caused by wires such as the sensing signal transistor SRT and the display write line GWL. The first organic layer 160 may be formed of an organic layer such as acryl resin, epoxy resin, phenolic resin, polyamide resin, polyimide resin and the like.

The light sensing element PD is formed on the first organic layer 160. To this end, the light sensing scan line FSL may be formed on the first organic layer 160. The light sensing scan line FSL may be formed as a single layer or multiple layers made of any one of molybdenum (Mo), aluminum (Al), chromium (Cr), gold (Au), titanium (Ti), nickel (Ni), neodymium (Nd), and copper (Cu) or an alloy thereof.

The second organic layer 161 for flattening a stepped portion may be formed on the first organic layer 160 and the light sensing scan line FSL. The second organic layer 161 may be formed of an organic layer such as acryl resin, epoxy resin, phenolic resin, polyamide resin, polyimide resin and the like.

A first contact hole CNT1 that exposes the light sensing scan line FSL is formed in the second organic layer 161. A sensing anode electrode SAND of the light sensing element PD may be connected to the light sensing scan line FSL, an anode voltage supply line, or the like through the first contact hole CNT1. Each of the light sensing elements PD may include the sensing anode electrode SAND, a PIN semiconductor layer PIN, and the cathode electrode 173. Here, the PIN semiconductor layer PIN may pass through a third organic layer 180 that covers the sensing anode electrode SAND to be electrically connected to the sensing anode electrode SAND.

The PIN semiconductor layer may include a P-type semiconductor layer connected to the sensing anode electrode SAND, an N-type semiconductor layer connected to the cathode electrode 173, and an I-type semiconductor layer disposed between the P-type semiconductor layer and the N-type semiconductor layer. In an embodiment, the I-type semiconductor layer is depleted by the P-type semiconductor layer and the N-type semiconductor layer to generate an electric field therein, and holes and electrons generated by light drift by the electric field. Due to this, the holes may be collected to the anode electrode through the P-type semiconductor layer and the electrons may be collected to the cathode electrode through the N-type semiconductor layer.

Figure 12:
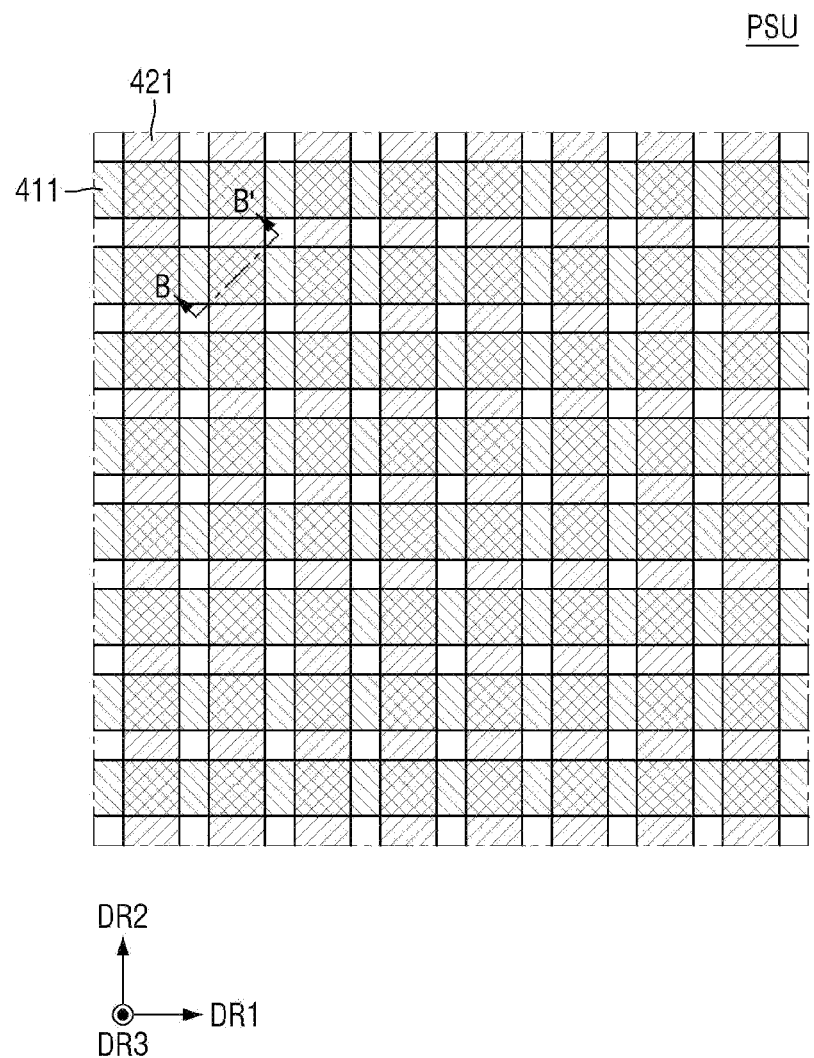
FIG. 12 is a layout diagram illustrating a planar structure of a pressure sensing unit shown in FIG. 3.
Figure 13:
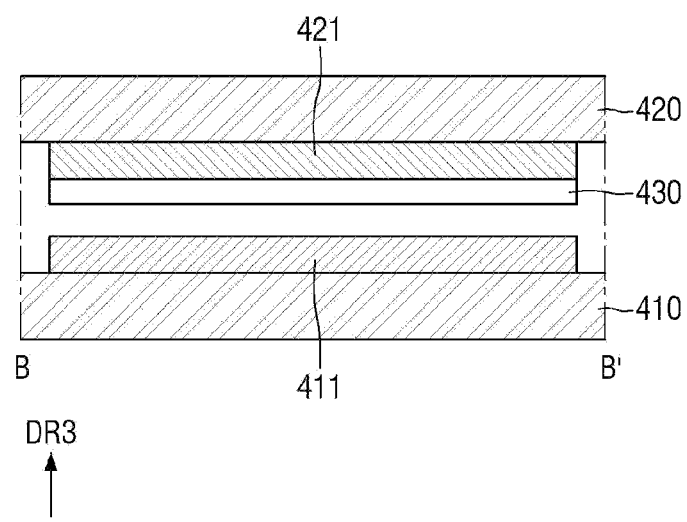
FIG. 13 is a cross-sectional view of a pressure sensing unit taken along line B-B' shown in FIG. 12.

FIG. 12 is a layout diagram illustrating a planar structure of a pressure sensing unit shown in FIG. 3. FIG. 13 is a cross-sectional view of a pressure sensing unit taken along line B-B' shown in FIG. 12.

Referring to FIGS. 12 and 13, when the pressure sensing unit PSU is disposed on the rear surface of the display panel 100, e.g., on the rear surface of the substrate SUB, pressure sensing electrodes of the pressure sensing unit PSU may overlap each of the display pixels and the light sensing pixels LSP formed in the front direction of the substrate SUB. Accordingly, they may be formed and disposed on the entire area of the substrate SUB in the rear direction.

The pressure sensing unit PSU may include a first base substrate 410, a first pressure sensor electrode 411, a second base substrate 420, a second pressure sensor electrode 421, and a pressure sensing layer 430 disposed between the first pressure sensor electrode 411 and the second pressure sensor electrode 421.

Each of the first base substrate 410 and the second base substrate 420 may include a polyethylene, polyimide, polycarbonate, polysulfone, polyacrylate, polystyrene, polyvinyl chloride, polyvinyl alcohol, polynorbornene, or polyester-based material. In an embodiment, each of the first base substrate 410 and the second base substrate 420 may be made of a polyethylene terephthalate (PET) film or a polyimide film.

The first base substrate 410 and the second base substrate 420 may be bonded to each other via a bonding layer. The bonding layer may include an adhesive material. The bonding layer may be disposed along the edges of the first base substrate 410 and the second base substrate 420, but the present disclosure is not limited thereto.

The first pressure sensor electrode 411 may be disposed on one surface of the first base substrate 410, which faces the second base substrate 420. The second pressure sensor electrode 421 may be disposed on one surface of the second base substrate 420, which faces the first base substrate 410. Each of the first pressure sensor electrode 411 and the second pressure sensor electrode 421 may include a conductive material. For example, each of the first pressure sensor electrode 411 and the second pressure sensor electrode 421 may be made of a metal such as silver (Ag) or copper (Cu), a transparent conductive oxide such as ITO, IZO, or ZIO, carbon nanotubes, conductive polymers, or the like. One of the first pressure sensor electrode 411 and the second pressure sensor electrode 421 may be a pressure driving electrode, and the other may be a pressure sensing electrode.

The pressure sensing layer 430 may be disposed between the first pressure sensor electrode 411 and the second pressure sensor electrode 421. The pressure sensing layer 430 may be in contact with at least one of the first pressure sensor electrode 411 or the second pressure sensor electrode 421. For example, the pressure sensing layer 430 may be in contact with the second pressure sensor electrode 421 as shown in FIG. 13, or alternatively, may be in contact with the first pressure sensor electrode 411. The first pressure sensor electrode 411 or the second pressure sensor electrode 421 may be pressure sensor electrodes.

The pressure sensing layer 430 may include a force sensitive material. The force sensitive material may contain metal nanoparticles formed of, for example, nickel, aluminum, tin, copper and the like, or carbon. The force sensitive material may be provided in polymer resin in the form of particles, but the present disclosure is not limited thereto. The pressure sensing layer 430 may be a force sensing layer.

When a force or pressure is applied to the pressure sensing unit PSU, the first pressure sensor electrode 411, the pressure sensing layer 430, and the second pressure sensor electrode 421 may be electrically connected with each other. According to the force or pressure applied to the pressure sensing unit PSU, electrical resistance of the pressure sensing layer 430 may become lower. The electrical resistance of the pressure sensing layer 430 may be calculated by applying a force driving voltage to the first pressure sensor electrode 411 and measuring a force sensing voltage through the second pressure sensor electrode 421. According to the electrical resistance of the pressure sensing layer 430, it is possible to determine whether a force or pressure has been applied or not and calculate the magnitude of the force pressure.

When the first pressure sensor electrode 411 and the second pressure sensor electrode 421 include an opaque conductive material or the pressure sensing layer 430 includes an opaque polymer resin, the pressure sensing unit PSU may be opaque.

Figure 14:
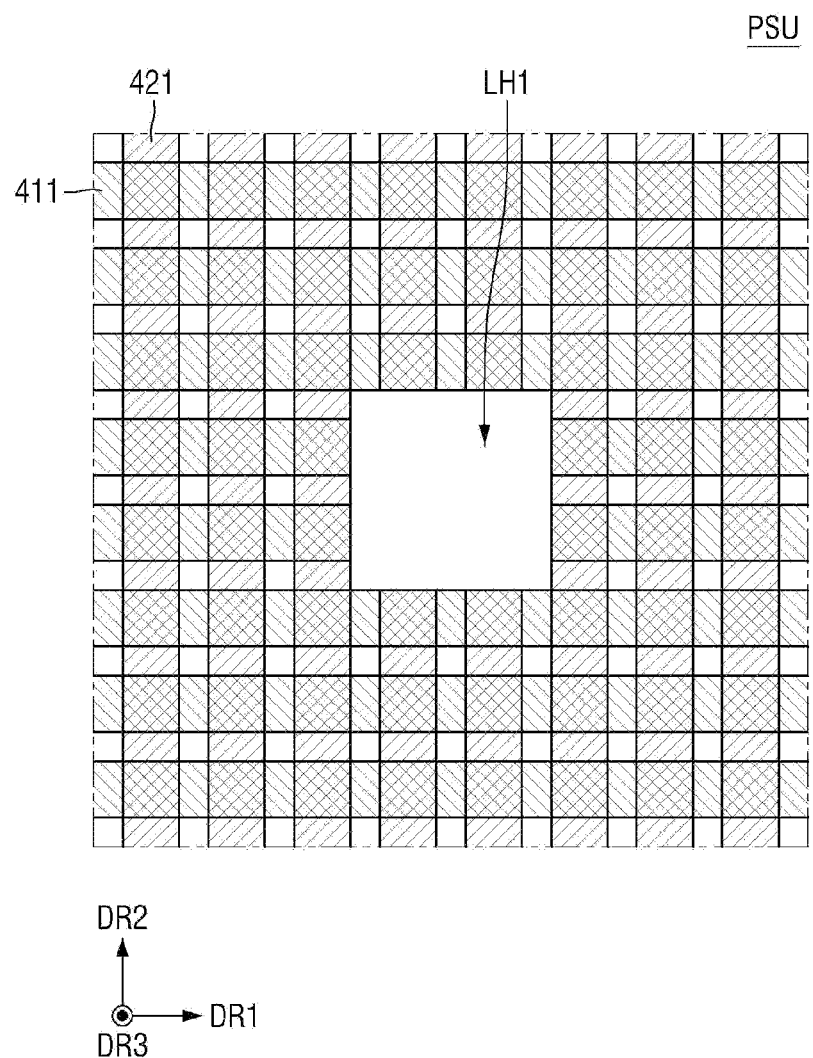
FIG. 14 is a layout diagram illustrating a planar structure of a pressure sensing unit shown in FIG. 4.

FIG. 14 is a layout diagram illustrating a planar structure of a pressure sensing unit shown in FIG. 4.

Referring to FIG. 14, when the pressure sensing unit PSU is disposed between the display panel 100 and the touch sensing unit TSU, the pressure sensing electrodes of the pressure sensing unit PSU may be formed to extend to a wiring region between the display pixels and the light sensing pixels LSP arranged in the display area DA so as not to overlap the display pixels and the light sensing pixels LSP.

To prevent light applied to the light sensing pixel PD from being blocked by the pressure sensing unit PSU, the pressure sensing unit PSU may include a first optical hole LH1. Among the first pressure sensor electrode 411, the second pressure sensor electrode 421, and the pressure sensing layer 430, a component including an opaque material may be removed from the first optical hole LH1. For example, when the first pressure sensor electrode 411 and the second pressure sensor electrode 421 include an opaque conductive material, the first pressure sensor electrode 411 and the second pressure sensor electrode 421 may be removed from the first optical hole LH1. When the force sensing layer 430 includes an opaque polymer resin, the force sensing layer 430 may be removed from the first optical hole LH1. When the first pressure sensor electrode 411 and the second pressure sensor electrode 421 include an opaque conductive material, and the force sensing layer 430 includes an opaque polymer resin, the first pressure sensor electrode 411, the second pressure sensor electrode 421, and the force sensing layer 430 may be removed from the first optical hole LH1.

FIGS. 12 and 14 illustrate eight first pressure sensor electrodes 411 and eight second pressure sensor electrodes 421 for simplicity of description, but the numbers of the first pressure sensor electrodes 411 and the second pressure sensor electrodes 421 are not limited thereto. The lengths of the pressure sensing unit PSU in the fourth direction DR4 and in the fifth direction DR5 may be in a range of about 10 mm to 20 mm. The lengths of the crossing region of the first pressure sensor electrode 411 and the second pressure sensor electrode 421 in the fourth direction DR4 and the fifth direction DR5 may be about 1.5 mm or more. The lengths of the first optical hole LH1 in the fourth direction DR4 and in the fifth direction DR5 may be about 3 mm or more.

Figure 15:
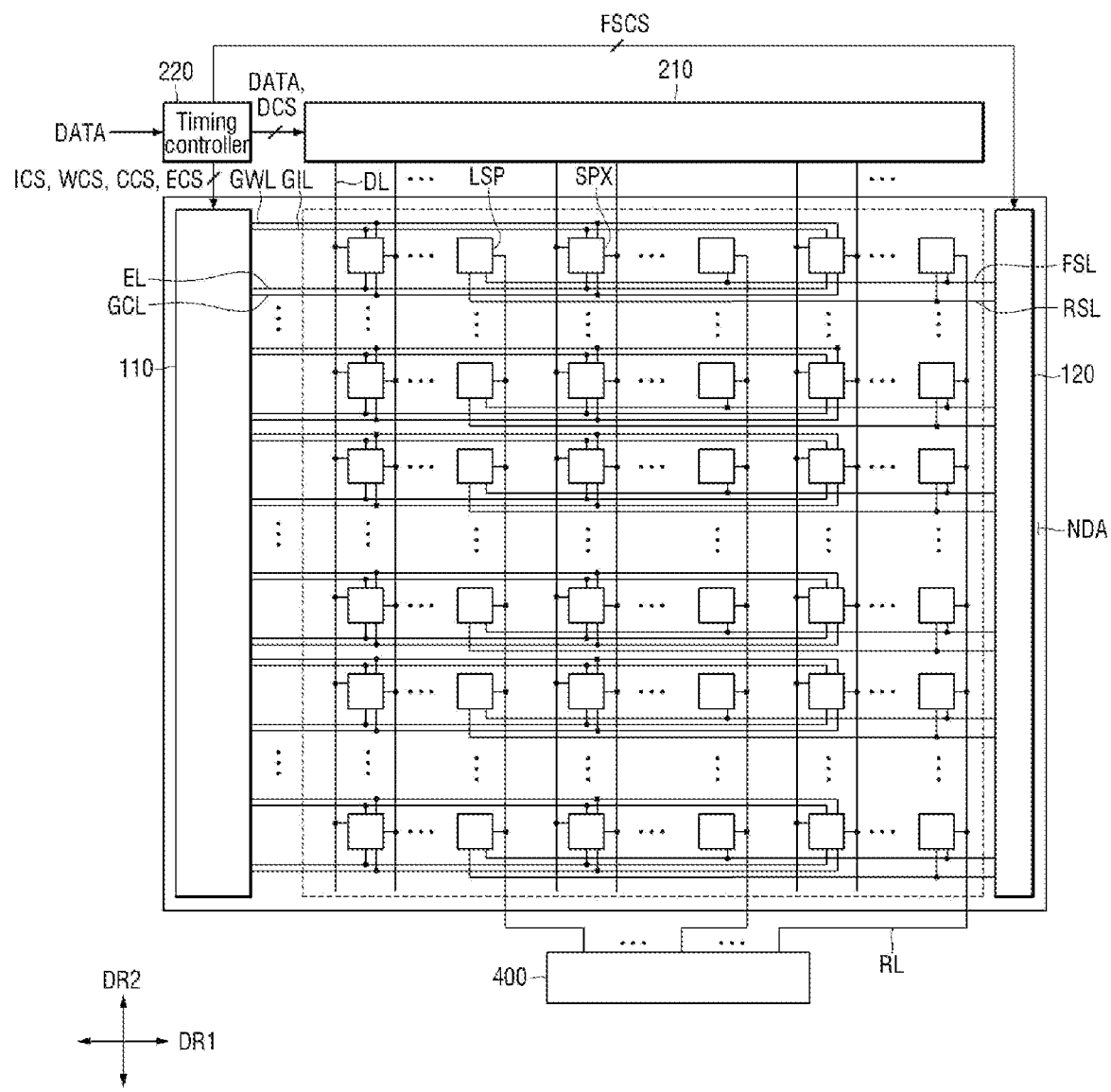
FIG. 15 is a configuration block diagram specifically illustrating a display device according to an embodiment of the present disclosure.
Figure 16:
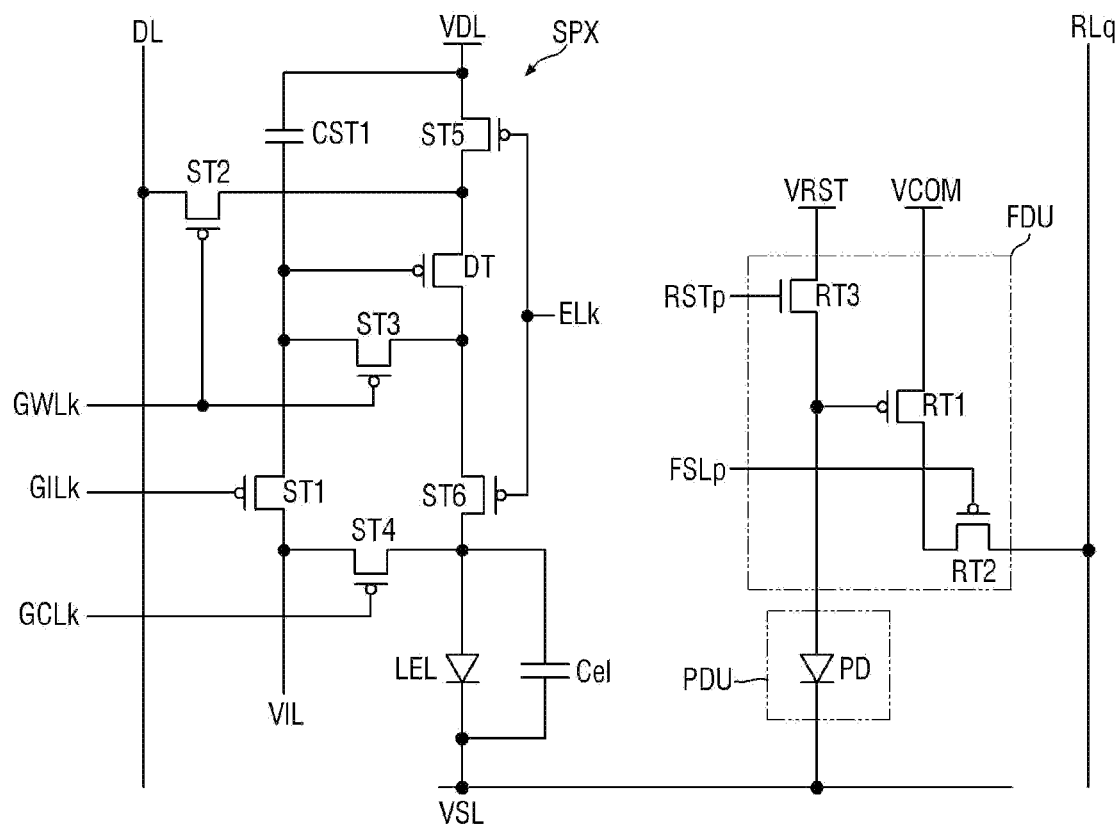
FIG. 16 is a circuit diagram illustrating a display pixel and a light sensing pixel according to an embodiment.

FIG. 15 is a configuration block diagram illustrating a display device according to an embodiment of the present disclosure. FIG. 16 is a circuit diagram illustrating a display pixel and a light sensing pixel according to an embodiment.

Referring to FIGS. 15 and 16, the light sensing pixels LSP arranged together with the display pixels SPX in the display area DA are each electrically connected to one of sensing reset lines RSL, one of the light sensing scan lines FSL, and one of the light sensing lines RL. Each of the light sensing pixels LSP may be reset by a reset signal from the sensing reset line RSL, and may transmit a light sensing signal to each light sensing line RL in response to the sensing scan signal from the light sensing scan line FSL.

As shown in FIG. 16, the light sensing pixels LSP may be divided into the light sensing portion PDU including the light sensing element PD, and the sensing driver FDU including first to third sensing transistors RT1 to RT3 and a sensing capacitor (not shown). Here, the sensing capacitor may be formed in parallel with the light sensing element PD.

The first sensing transistor RT1 of the sensing driver FDU may allow a light sensing current to flow according to the voltages of the light sensing element PD and the sensing capacitor. The amount of the light sensing current may vary depending on a voltage applied to the light sensing element PD and the sensing capacitor. The gate electrode of the first sensing transistor RT1 may be connected to the second electrode of the light sensing element PD. The first electrode of the first sensing transistor RT1 may be connected to a common voltage source Vcom to which a common voltage is applied. The second electrode of the first sensing transistor RT1 may be connected to the first electrode of the second sensing transistor RT2.

When the sensing scan signal FSp of a gate-on voltage is applied to the light sensing scan line FSL, the second sensing transistor RT2 may allow the sensing current of the first sensing transistor RT1 to flow to the light sensing line RLq. In this case, the light sensing line RLq may be charged with a sensing voltage by the sensing current. The gate electrode of the second sensing transistor RT2 may be connected to the light sensing scan line FSL, the first electrode thereof may be connected to the second electrode of the first sensing transistor RT1, and the second electrode thereof may be connected to the light sensing line RLq.

When a reset signal of the gate-on voltage is applied to the sensing reset line RSL, the third sensing transistor RT3 may reset the voltages of the light sensing element PD and the sensing capacitor to a reset voltage of a reset voltage source VRST. The gate electrode of the third sensing transistor RT3 may be connected to the sensing reset line RSL, the first electrode thereof may be connected to the reset voltage source VRST, and the second electrode thereof may be connected to the second electrode of the light sensing element PD.

It is illustrated in FIG. 16 that the first sensing transistor RT1 and the second sensing transistor RT2 are formed of a P-type metal oxide semiconductor field effect transistor (MOSFET), and the third sensing transistor RT3 is formed of an N-type MOSFET. However, embodiments of the present disclosure are not limited thereto, and they may be selectively formed in the same type or different types. Further, any one of the first electrode and the second electrode of each of the first sensing transistor RT1, the second sensing transistor RT2, and the third sensing transistor RT3 may the source electrode and the other one may be the drain electrode.

The plurality of sensing stages FTA1 to FTAi included in the light sensing driver 120 sequentially supplies the sensing scan signals and the sensing reset signals to the sensing drivers FDU connected to the light sensing portions PDU in the display area DA. Accordingly, the number of the light sensing scan lines FSL and the number of the sensing reset lines RSL may be the same as the number of the display write lines GWL.

Figure 17:
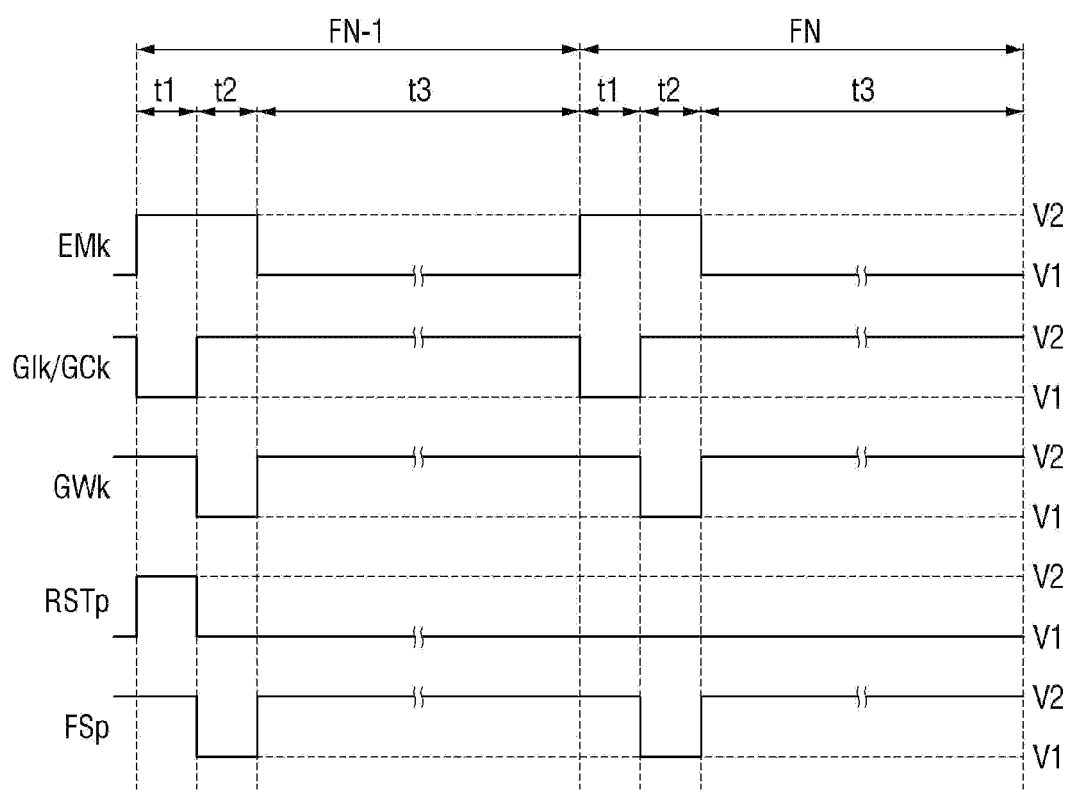
FIG. 17 is a waveform diagram illustrating a sensing scan signal and a reset signal inputted to a first display pixel of a display pixel and a light sensing pixel according to an embodiment.

FIG. 17 is a waveform diagram illustrating a sensing scan signal and a reset signal inputted to a first display pixel of a display pixel and a light sensing pixel according to an embodiment.

FIG. 17 shows the $k^{th}$ display emission signal EMk applied to the $k^{th}$ emission line ELk, the $k^{th}$ display initialization signal GIk applied to the $k^{th}$ display initialization line GILk, the $k^{th}$ display control signal GCk applied to the $k^{th}$ display control line GCLk, the $k^{th}$ display scan signal GWk applied to the $k^{th}$ display write line GWLk, a $p^{th}$ reset signal RSTp applied to a $p^{th}$ sensing reset line RSLp, and the $p^{th}$ sensing scan signal FSp applied to the $p^{th}$ light sensing scan line FSLp, during the $(N-1)^{th}$ frame period FN−1 and the $N^{th}$ frame period FN.

The $p^{th}$ reset signal RSTp applied to the $p^{th}$ sensing reset line RSLp is a signal for controlling turning on/off of the third sensing transistor RT3, and the $p^{th}$ sensing scan signal FSp applied to the $p^{th}$ light sensing scan line FSLp is a signal for controlling turning on/off of the second sensing transistor RT2.

The $p^{th}$ reset signal RSTp is generated at the second level voltage V2 during the first period t1 and is generated at the first level voltage V1 during the second period t2 and the third period t3. In addition, the $p^{th}$ sensing scan signal FSp is generated at the first level voltage V1 during the second period t2 and the second level voltage V2 during the first period t1 and the third period t3. The $p^{th}$ sensing scan signal FSp may be applied at the same timing as that of the $k^{th}$ display scan signal GWk.

During the first period t1, the $p^{th}$ reset signal RSTp of the second level voltage V2 is supplied to the gate electrode of the third sensing transistor RT3. Accordingly, the third sensing transistor RT3 is turned on by the $p^{th}$ reset signal RSTp of the second level voltage V2 to reset the second electrode of the light sensing element PD to a reset voltage of the reset voltage source VRST. On the other hand, the $p^{th}$ sensing scan signal FSp having the second level voltage V2 is supplied to the gate electrode of the second sensing transistor RT2. The second sensing transistor RT2 is turned off by the $p^{th}$ sensing scan signal FSp having the second level voltage V2.

During the second period t2 and the third period t3, the $p^{th}$ reset signal RSTp of the first level voltage V1 is supplied to the gate electrode of the third sensing transistor RT3. Accordingly, the third sensing transistor RT3 maintains a turned-off state. On the other hand, during the second period t2, the $p^{th}$ sensing scan signal FSp of the first level voltage V1 is supplied to the gate electrode of the second sensing transistor RT2. Therefore, the second sensing transistor RT2 may be turned on during the second period t2, and the third sensing transistor RT3 may be turned off during the second period t2 and the third period t3. In particular, the voltage of the sensing anode electrode of the light sensing element PD may increase according to the light incident on the front surface during the third period t3.

Figure 18:
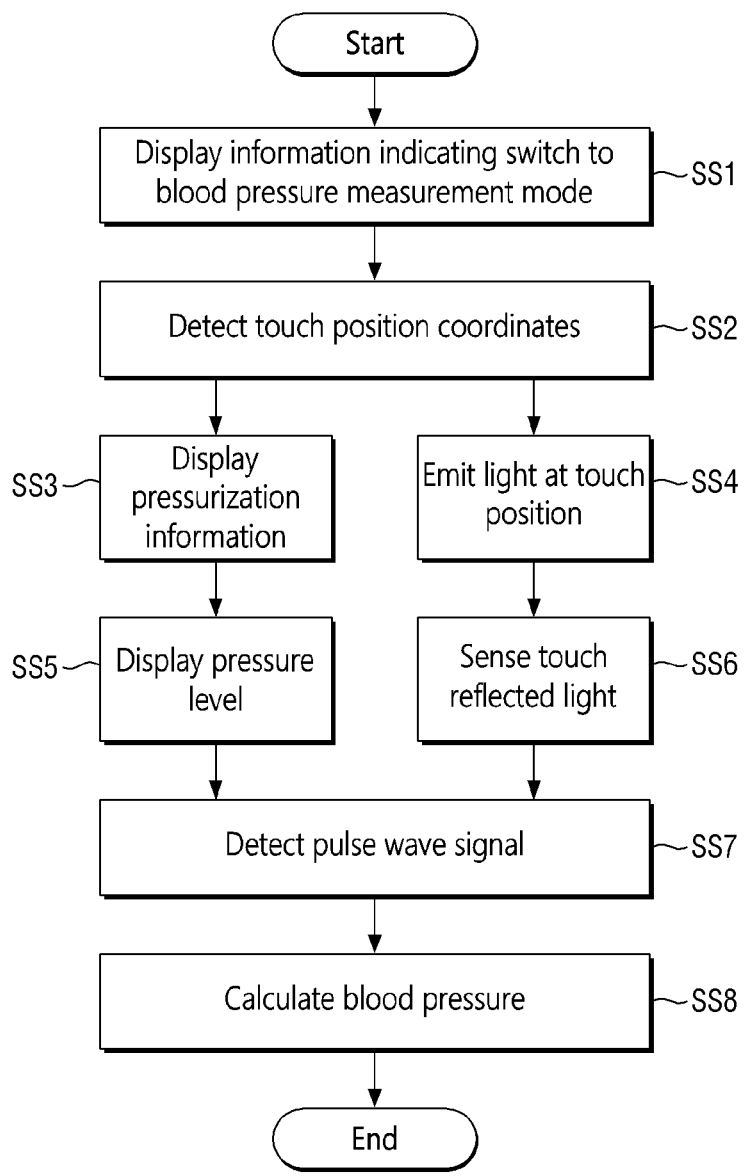
FIG. 18 is a flowchart illustrating a method of measuring blood pressure by a display device according to an embodiment.
Figure 19:
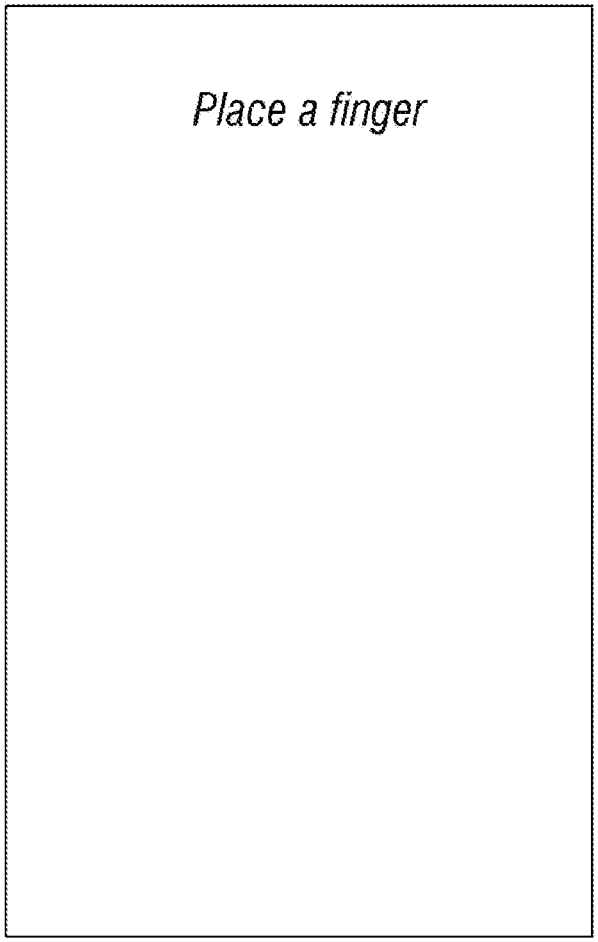
FIG. 19 is a diagram illustrating an image display screen when switching to a blood pressure measurement mode according to an embodiment.

FIG. 18 is a flowchart illustrating a method of measuring blood pressure by a display device according to an embodiment. FIG. 19 is a diagram illustrating an image display screen when switching to a blood pressure measurement mode according to an embodiment.

Referring to FIGS. 18 and 19, the display driving circuit 200 in a state such as an image display mode or power saving or standby mode may be switched to a blood pressure measurement mode according to an operation such as a user's selection of a blood pressure measurement function and execution of an application.

When switched to the blood pressure measurement mode, the timing controller 220 of the display driving circuit 200 controls the data driver 210 and the display scan driver 110 to display information indicating that the mode has been switched to the blood pressure measurement mode on the display area DA (step SS1). In particular, the display driving circuit 200 may show that the mode has been switched to the blood pressure measurement mode by displaying a guide phrase such as inducing a user to touch the display panel 100 with his/her body part such as a finger. In this case, the display driving circuit 200 does not predesignate a touch position of a body part such as a finger to display or guide it through an image. Accordingly, when the user confirms that the mode has been switched to the blood pressure measurement mode, the user may be allowed to comfortably touch any position on the display panel 100 with his/her finger or the like.

In the blood pressure measurement mode, the touch driver 500 may receive touch sensing signals in real time through the touch sensing unit TSU of the display panel 100 to detect touch data and touch coordinate data. The touch driver 500 may transmit the touch data and the touch coordinate data detected in real time to the timing controller 220 (step SS2).

Figure 20:
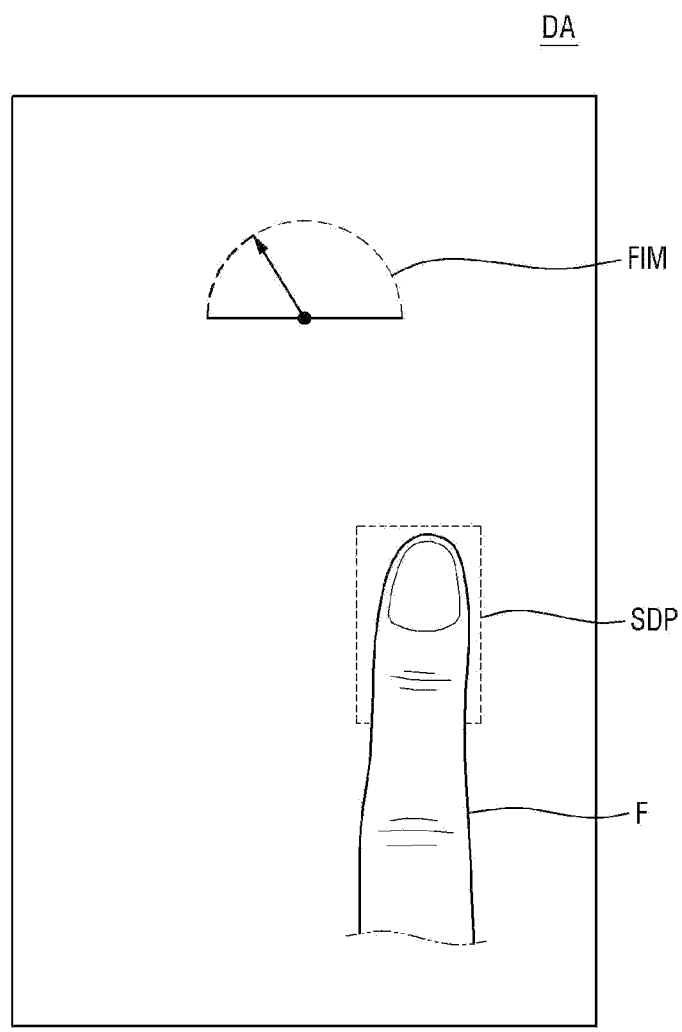
FIG. 20 is a diagram illustrating an image display screen during a blood pressure detection period according to an embodiment.

FIG. 20 is a diagram illustrating an image display screen during a blood pressure detection period according to an embodiment.

Referring to FIG. 20, the timing controller 220 displays a preset pressurization information display image FIM on the display area DA through an option, and may receive pressure data in real time to indicate a change in the level of the pressure applied by the user through the pressurization information display image FIM (step SS3).

The timing controller 220 detects and sets a body part touch area SDP of a body part such as a finger F based on the touch data and the touch coordinate data. In addition, the timing controller 220 controls the data driver 210 and the display scan driver 110 to allow the display pixels SPX of the body part touch area SDP to emit light with a preset brightness (step SS4). To this end, the timing controller 220 may align grayscale data preset for blood pressure detection according to the position of the body part touch area SDP and may supply it to the data driver 210. In addition, by controlling the driving timings of the data driver 210 and the display scan driver 110, the timing controller 220 may allow the display pixels SPX of the body part touch area SDP to emit light.

The timing controller 220 controls the light sensing driver 120 to supply the sensing scan signals FSp to the sensing driver FDU of the light sensing pixel LSP. In addition, the timing controller 220 supplies the coordinate information on the body part touch area SDP to the blood pressure detection circuit 400.

The touch driver 500 may receive pressure sensing signals in real time through the pressure sensing unit PSU of the display panel 100, and generate pressure data according to a change in the pressure level through the pressure sensing signals to transmit the pressure data to the timing controller 220. Accordingly, the timing controller 220 may display the pressure variation according to the pressure data through the pressurization information display image FIM in real time (step SS5).

Meanwhile, light emitted from the display pixels SPX arranged in the body part touch area SDP may be reflected from the user's body part such as the finger F, and may be sensed through the light sensing portion PDU of the light sensing pixel LSP. Accordingly, based on the coordinate information on the body part touch area SDP inputted from the timing controller 220, the blood pressure detection circuit 400 receives the light sensing signals from the light sensing lines RL corresponding to the body part touch area SDP. Then, the blood pressure detection circuit 400 converts the received light sensing signals into digital data signals (step SS6).

Figure 21:
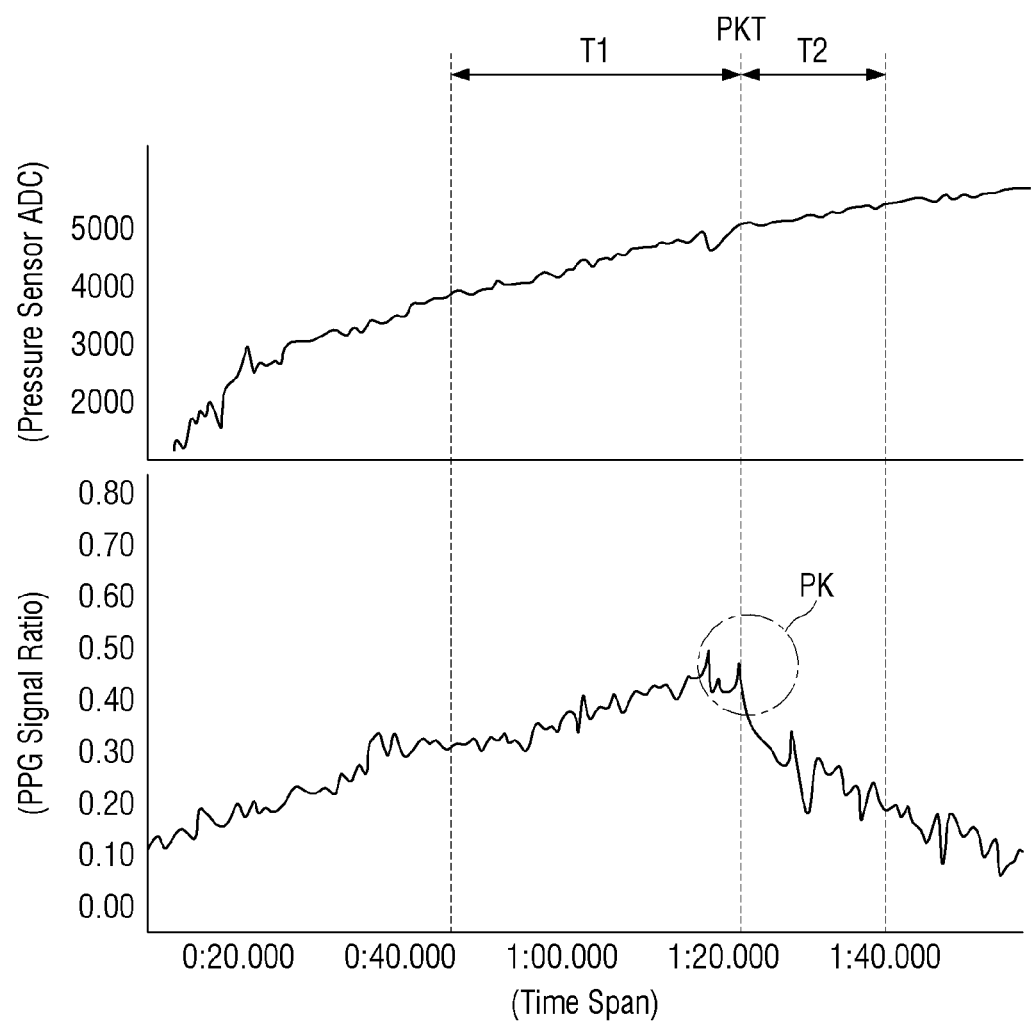
FIG. 21 is a graph illustrating a blood pressure calculation method of a blood pressure detection circuit according to an embodiment.

FIG. 21 is a graph illustrating a blood pressure calculation method of a blood pressure detection circuit according to an embodiment.

Referring to FIG. 21, during the systole of the heart, the blood ejected from the left ventricle of the heart moves to the peripheral tissues, and thus the blood volume in the arterial side increases. Further, when the heart contracts, red blood cells carry more oxygen hemoglobin to the peripheral tissues. When the heart relaxes, the heart receives a partial influx of blood from the peripheral tissues. When light is irradiated to peripheral blood vessels, the irradiated light is absorbed by the peripheral tissues. Light absorbance depends on hematocrit and blood volume. The light absorbance may have a maximum value when the heart contracts and may have a minimum value when the heart relaxes. Therefore, light sensed by the light sensing element PD may be the least when the heart contracts and may be the most when the heart relaxes.

Further, when the user puts a finger F on the display panel 100 and lifts it off in the blood pressure measurement mode, a force (contact force) applied to the pressure sensing unit PSU may gradually increase to reach a maximum value, and then may gradually decrease. When the contact force increases, blood vessels may be narrowed, resulting in no blood flow. When the contact force decreases, the blood vessels expand, and thus blood flows again. A further decrease of the contact force results in greater blood flow. Therefore, the change in the amount of light sensed by the light sensing element PD may be proportional to the change in blood flow. Accordingly, the blood pressure detection circuit 400 generates a pulse wave signal according to the pressure applied by the user, based on a digitally converted pressure data value (ADC of the pressure sensing unit) calculated by the pressure sensing unit PSU and an optical signal (PPG signal ratio) according to the amount of light sensed by the light sensing element PD (step SS7). The pulse wave signal may have a waveform that vibrates according to a heartbeat cycle.

The blood pressure detection circuit 400 may estimate blood pressures of the blood vessels of the finger F based on time differences between time points PKT corresponding to peaks PK of the calculated pulse wave signal and time points corresponding to peaks of the filtered pulse wave. Specifically, the blood pressure detection circuit 400 may calculate pulse wave signals during preset periods T1 and T2 before and after the time points PKT corresponding to the peaks PK of the calculated pulse wave signal, and may detect blood pressure according to differences between the pulse wave signals. Among the estimated blood pressure values, a maximum blood pressure value may be determined as a systolic blood pressure value, and a minimum blood pressure value may be determined as a diastolic blood pressure value. Further, additional blood pressure values such as an average blood pressure value or the like may be calculated using the estimated blood pressure values. The timing controller 220 displays the detected blood pressure information on the display area DA (step SS8).

The method for measuring the blood pressure described above is only exemplary, various other methods are disclosed in Korean Patent Application Publication No. 10-2018-0076050, Korean Patent Application Publication No. 10-2017-0049280, and Korean Patent Application Publication No. 10-2019-0040527, the disclosures of which are incorporated herein by reference in their entirety as fully disclosed herein.

In this way, the timing controller 220 of the display driving circuit 200 may receive touch coordinate data through the touch driver 500 to detect and set the body part touch area SDP, without guiding the touch position of the body part through an image in the blood pressure measurement mode. In addition, the timing controller 220 may control the display pixels SPX and the light sensing pixels LSP in the body part touch area SDP to be driven. Accordingly, based on the coordinate information on the body part touch area SDP inputted from the timing controller 220, the blood pressure detection circuit 400 may detect the user's blood pressure through the body part touched on the body part touch area SDP.

While, the user's finger F is exemplified as the user's body part whose blood pressure is measured in FIGS. 18 to 21, but the present disclosure is not limited thereto. For example, the user's body whose blood pressure is measured may be a wrist or another body part where blood vessels exist.

Figure 22:
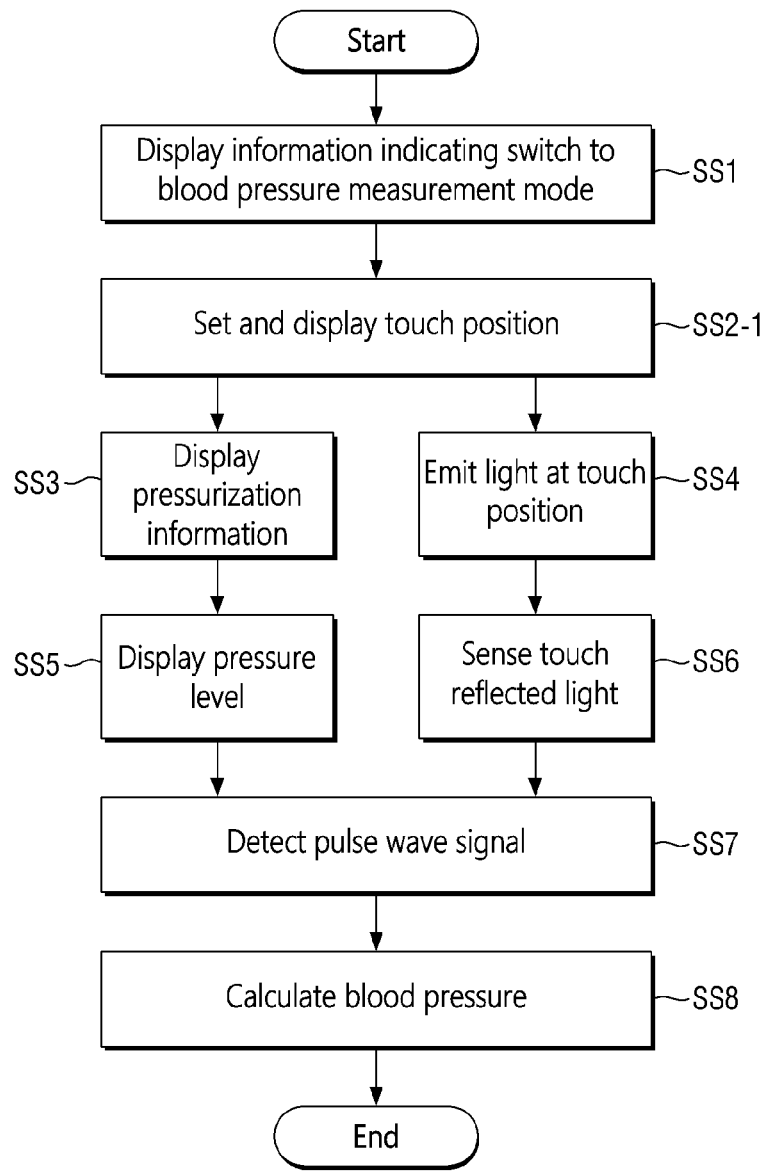
FIG. 22 is a flowchart illustrating a method of measuring blood pressure by a display device according to an embodiment of the present disclosure.
Figure 23:
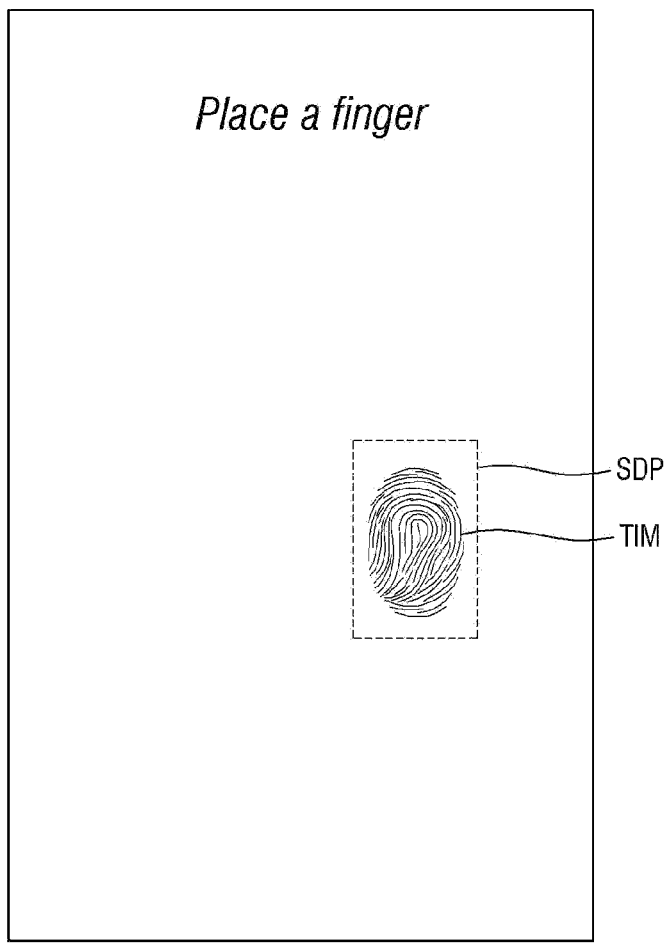
FIG. 23 is a diagram illustrating an image display screen when switching to a blood pressure detection mode according to an embodiment.

FIG. 22 is a flowchart illustrating a method of measuring blood pressure by a display device according to an embodiment of the present disclosure. FIG. 23 is a diagram illustrating an image display screen when switching to a blood pressure detection mode according to an embodiment.

Referring to FIGS. 22 and 23, when the mode is switched to the blood pressure measurement mode, the timing controller 220 of the display driving circuit 200 controls the data driver 210, the display scan driver 110, and the like to display information indicating that the mode has been switched to the blood pressure measurement mode on the display area DA (step SS1).

The display driving circuit 200 may display a guide phrase for inducing the user to touch the display panel 100 with his/her body part such as a finger to inform that the mode has been switched to the blood pressure measurement mode. In an embodiment, the display driving circuit 200 randomly sets the size of the body part touch area SDP and the arrangement position of the touch area SDP, and controls the data driver 210 and the display scan driver 110 to display the randomly set touch area SDP and a touch inducing image TIM on the display area DA (step SS2-1). To this end, the display driving circuit 200 may align the data of the touch inducing image TIM according to the randomly set touch area SDP and supply it to the data driver 210, and may supply the write control signal WCS to the display scan driver 110. As shown in FIG. 23, if the body part touch area SDP is randomly changed and set, it may be possible to prevent problems such as deterioration caused by repetitive blood pressure detection in one area.

Figure 24:
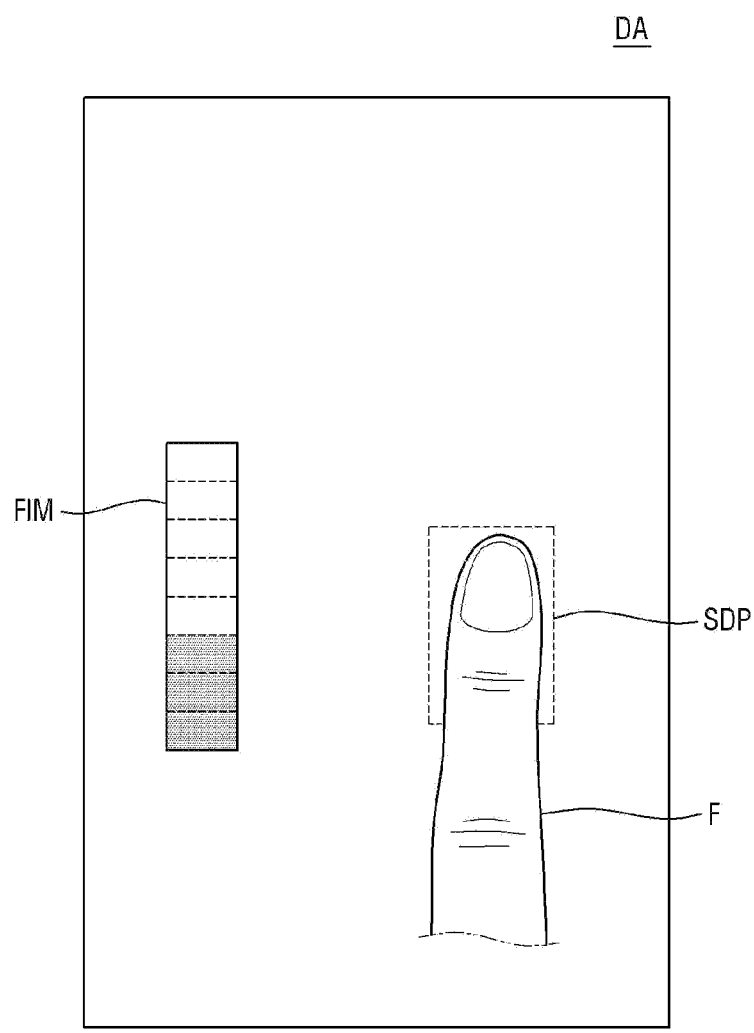
FIG. 24 is a diagram illustrating an image display screen during a blood pressure detection period according to an embodiment.

FIG. 24 is a diagram illustrating an image display screen during a blood pressure detection period according to an embodiment.

Referring to FIG. 24, the timing controller 220 displays the preset pressurization information display image FIM on the display area DA through an option, and may receive pressure data in real time to display a change in the level of the pressure applied by the user through the pressurization information display image FIM (step SS3).

To detect blood pressure, the timing controller 220 controls the data driver 210 and the display scan driver 110 to allow the display pixels SPX of the randomly set touch area SDP to emit light with a preset brightness. To this end, the timing controller 220 may align grayscale data preset for blood pressure detection according to the position of the body part touch area SDP and may supply it to the data driver 210. In addition, by controlling the driving timings of the data driver 210 and the display scan driver 110, the timing controller 220 may allow the display pixels SPX of the body part touch area SDP to emit light.

The timing controller 220 controls the light sensing driver 120 to supply the sensing scan signals FSp to the sensing driver FDU of the light sensing pixel LSP. In addition, the timing controller 220 supplies the coordinate information on the body part touch area SDP to the blood pressure detection circuit 400.

The touch driver 500 may receive pressure sensing signals in real time through the pressure sensing unit PSU of the display panel 100, and generate pressure data according to a change in the pressure level through the pressure sensing signals to transmit the pressure data to the timing controller 220. Accordingly, the timing controller 220 may display the pressure variation according to the pressure data through the pressurization information display image FIM in real time (step SS5).

Light emitted from the display pixels SPX arranged in the body part touch area SDP may be reflected from the user's body part such as the finger F, and may be sensed through the light sensing portion PDU of the light sensing pixel LSP. Accordingly, the blood pressure detection circuit 400 receives the light sensing signals from the light sensing lines RL corresponding to the body part touch area SDP, based on the coordinate information on the body part touch area SDP. Then, the blood pressure detection circuit 400 converts the received light sensing signals into digital data signals (step SS6).

The blood pressure detection circuit 400 generates a pulse wave signal based on the pressure data calculated by the pressure sensing unit PSU and the optical signal (PPG signal ratio) sensed by the light sensing element PD (step SS7). Thereafter, the blood pressure detection circuit 400 detects (or calculates) blood pressure according to the variation magnitude of the pulse wave signals, and the timing controller 220 displays the detected blood pressure information on the display area DA (step SS8).

Figure 25:
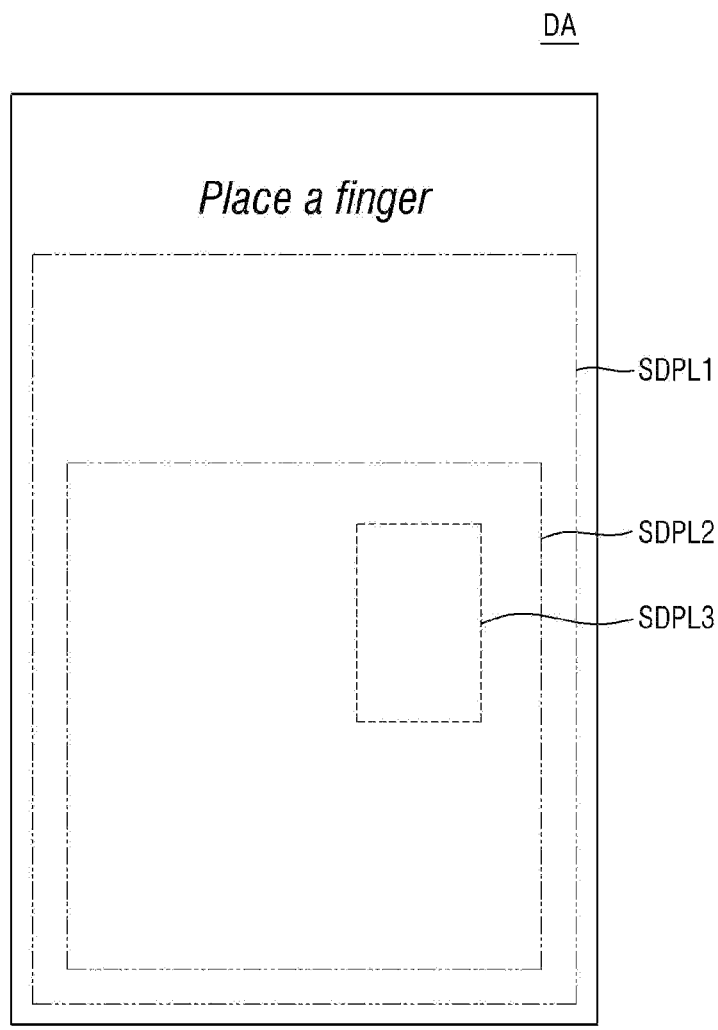
FIG. 25 is a diagram illustrating an image display screen when switching to a blood pressure detection mode according to an embodiment.

FIG. 25 is a diagram illustrating an image display screen when switching to a blood pressure detection mode according to an embodiment.

Referring to FIG. 25, when the mode is switched to the blood pressure measurement mode, the timing controller 220 of the display driving circuit 200 controls the data driver 210, the display scan driver 110, and the like to display a guide phrase for inducing the user to touch the display area DA with his/her body part. In an embodiment, the display driving circuit 200 randomly converts and set the size of the touch area SDP and the arrangement position of the touch area SDP, and may control the data driver 210 and the display scan driver 110 to display boundary lines SDPL1 to SDPL3 of the randomly set touch area SDP on the display area DA.

As shown in FIG. 25, if the size of the body part touch area SDP and the arrangement position of the touch area SDP are randomly changed and set, it may be possible to prevent problems such as deterioration caused by repetitive blood pressure detection in one area.

Figure 26:
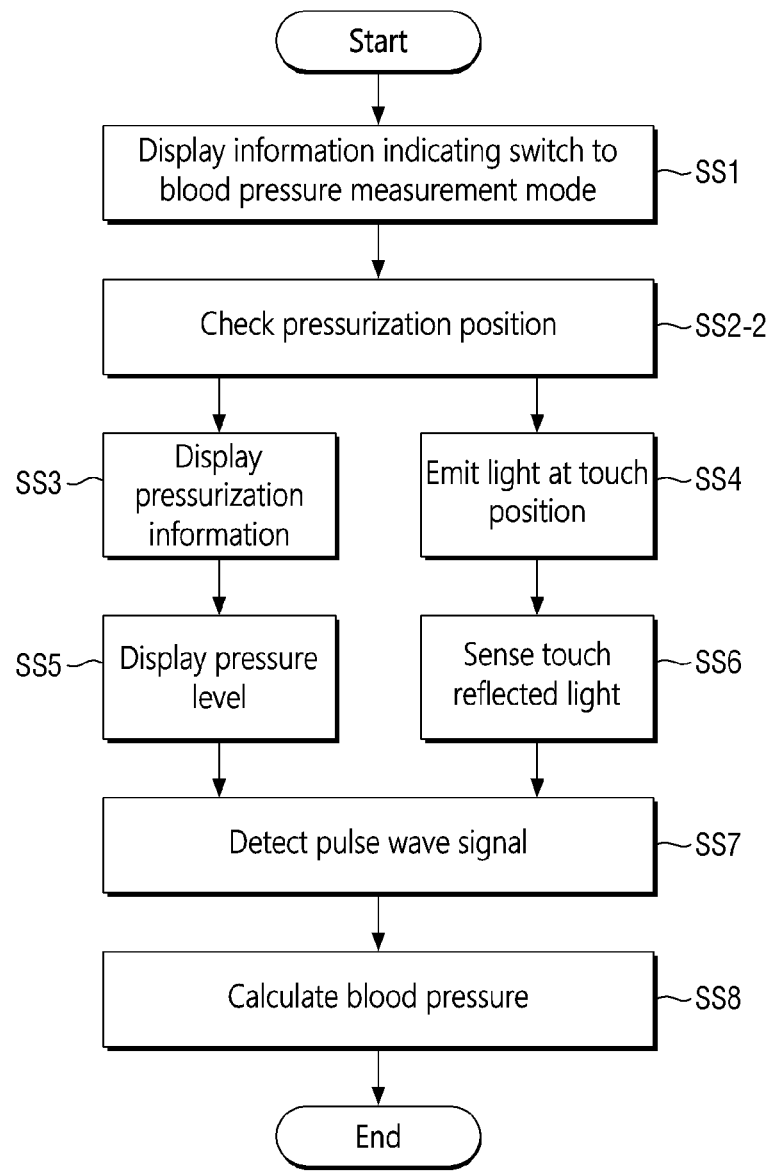
FIG. 26 is a flowchart illustrating a method of measuring blood pressure by a display device according to an embodiment of the present disclosure.
Figure 27:
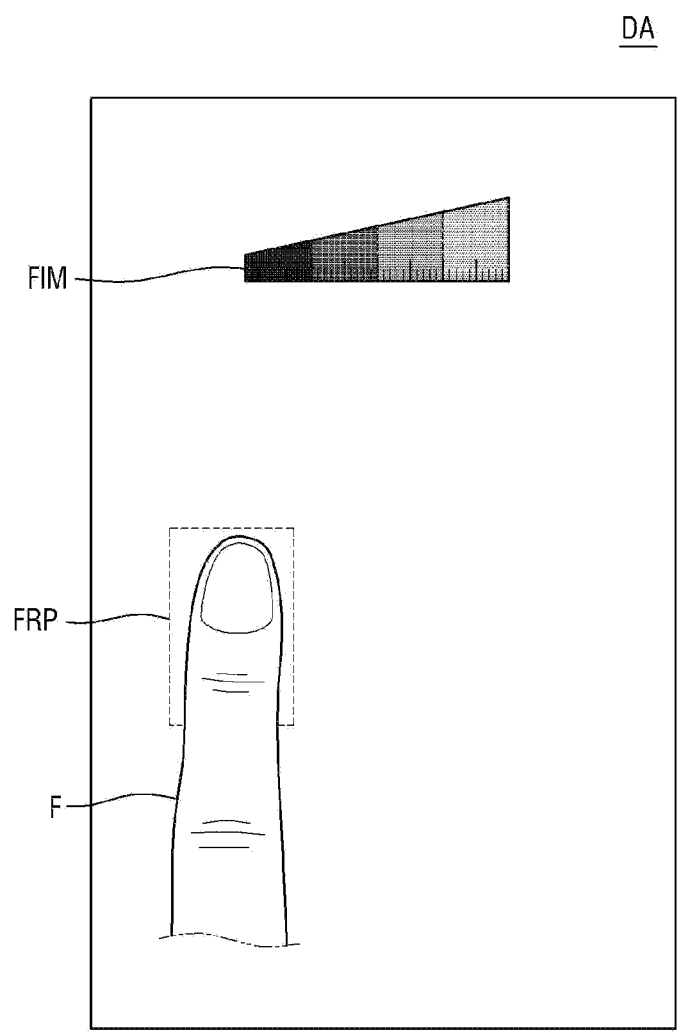
FIG. 27 is another diagram illustrating an image display screen of a blood pressure detection period according to an embodiment.

FIG. 26 is a flowchart illustrating a method of measuring blood pressure by a display device according to an embodiment of the present disclosure. FIG. 27 is another diagram illustrating an image display screen of a blood pressure detection period according to an embodiment.

Referring to FIGS. 26 and 27, when the mode is switched to the blood pressure measurement mode, the timing controller 220 of the display driving circuit 200 controls the data driver 210, the display scan driver 110, and the like to display information indicating that the mode has been switched to the blood pressure measurement mode on the display area DA (step SS1).

The display driving circuit 200 may display a guide phrase for inducing the user to touch the display panel 100 with his/her body part such as a finger to inform that the mode has been switched to the blood pressure measurement mode. In this case, the display driving circuit 200 may allow the user to comfortably touch any position on the display panel 100 with his/her finger or the like, without guiding the touch position of a body part such as a finger through an image or sound.

In the blood pressure measurement mode, the touch driver 500 may receive pressure sensing signals in real time through the pressure sensing unit PSU of the display panel 100 to detect pressure data and pressure sensing coordinate data. The touch driver 500 transmits the pressure data and the detected pressure sensing coordinate data to the timing controller 220 (step SS2-2). The pressure sensing coordinate data may be detected in real time. The touch driver 500 may receive the pressure sensing signals at a pressurization position of the touched position.

Referring to FIG. 27, the timing controller 220 displays the preset pressurization information display image FIM on the display area DA through an option, and may receive the pressure data in real time to indicate a change in the level of the pressure applied by the user through the pressurization information display image FIM (step SS3). The pressurization information display image FIM may be displayed in a preset and predesigned type such as a bar block type, a bar gauge type, a circular gauge type, a polygonal figure size type, a polygonal figure gauge type, a polygonal figure block type, a bar graph type, or an arrow gauge type.

The timing controller 220 detects and sets the touch area SDP of a body part such as the finger F based on the pressure data and the pressure sensing coordinate data. In addition, the timing controller 220 controls the data driver 210 and the display scan driver 110 to allow the display pixels SPX of the body part touch area SDP to emit light with a preset brightness. In addition, the timing controller 220 controls the light sensing driver 120 to supply the sensing scan signals FSp to the sensing driver FDU of the light sensing pixel LSP. In addition, the timing controller 220 supplies the coordinate information on the body part touch area SDP to the blood pressure detection circuit 400. In addition, the timing controller 220 may display the pressure variation according to the pressure data through the pressurization information display image FIM in real time (step SS5).

The blood pressure detection circuit 400 receives the light sensing signals from the light sensing lines RL corresponding to the body part touch area SDP, based on the coordinate information on the body part touch area SDP. Then, the blood pressure detection circuit 400 converts the received light sensing signals into digital data signals (step SS6).

The blood pressure detection circuit 400 generates a pulse wave signal based on the optical signal (PPG signal ratio), and detects blood pressure according to the variation magnitude of the pulse wave signals, and the timing controller 220 displays the detected blood pressure information on the display area DA (steps SS7 and SS8).

As described above, the display driving circuit 200 may randomly set the size of the body part touch area SDP and the arrangement position of the touch area SDP, and induce blood pressure detection to be performed in the randomly set touch area SDP, thereby preventing deterioration in any one area that may occur when the blood pressure is detected.

Figure 28:
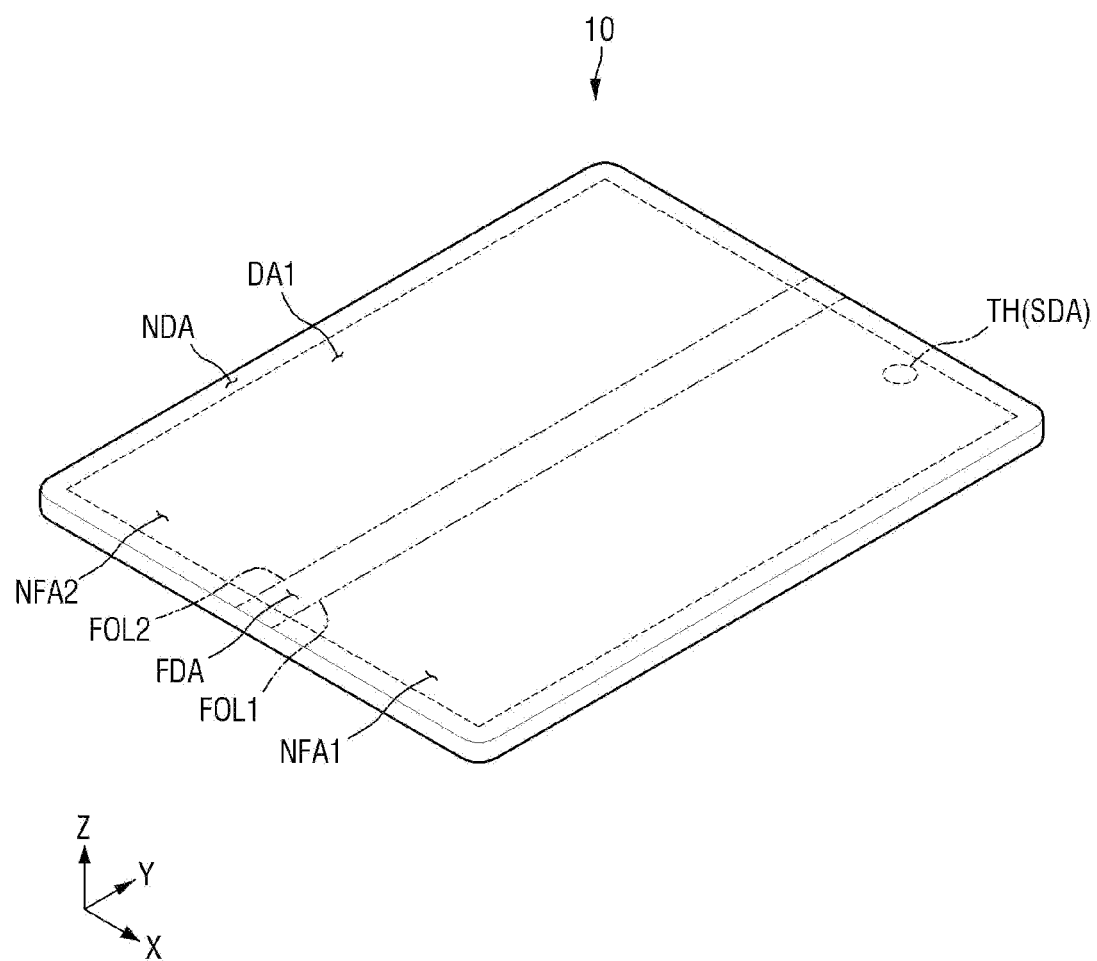
FIGS. 28 and 29 are perspective views illustrating a display device according to an embodiment of the present disclosure.
Figure 29:
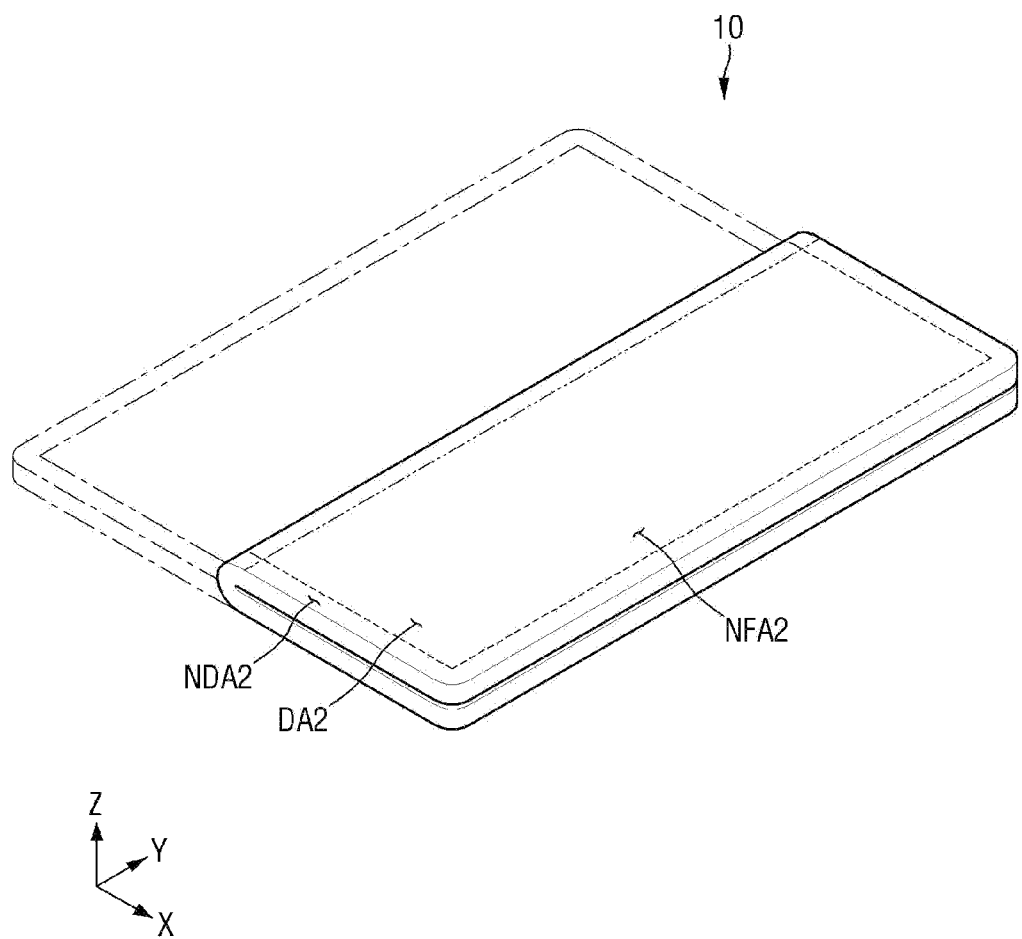

FIGS. 28 and 29 are perspective views illustrating a display device according to an embodiment of the present disclosure.

FIGS. 28 and 29 illustrate the display device 10 as a foldable display device that is folded in the first direction (X-axis direction). The display device 10 may maintain a folded state or an unfolded state. The display device 10 may be folded in an in-folding manner in which the front surface is disposed on the inside thereof. When the display device 10 is bent or folded in the in-folding manner, the front surfaces of the display device 10 may be disposed to face each other. Alternatively, the display device 10 may be folded in an out-folding manner in which the front surface is disposed on the outside thereof. When the display device 10 is bent or folded in an out-folding manner, the rear surfaces of the display device 10 may be disposed to face each other.

A first non-folding area NFA1 may be disposed on one side, for example, the right side of a folding area FDA. A second non-folding area NFA2 may be disposed on the other side, for example, the left side of the folding area FDA. The touch sensing unit TSU according to an embodiment of the present disclosure may be disposed on each of the first non-folding area NFA1 and the second non-folding area NFA2.

A first folding line FOL1 and a second folding line FOL2 extend in the second direction (Y-axis direction), and the display device 10 may be folded in the first direction (X-axis direction). Accordingly, the length of the display device 10 in the first direction (X-axis direction) may be reduced to approximately half, so that a user can conveniently carry the display device 10.

However, the extension direction of the first folding line FOL1 and the extension direction of the second folding line FOL2 are not limited to the second direction (Y-axis direction). For example, the first folding line FOL1 and the second folding line FOL2 may extend in the first direction (X-axis direction), and the display device 10 may be folded in the second direction (Y-axis direction). In this case, the length of the display device 10 in the second direction (Y-axis direction) may be reduced to approximately half. Alternatively, the first folding line FOL1 and the second folding line FOL2 may extend in the diagonal direction of the display device 10 between the first direction (X-axis direction) and the second direction (Y-axis direction). In this case, the display device 10 may be folded in a triangular shape.

When the first folding line FOL1 and the second folding line FOL2 extend in the second direction (Y-axis direction), the length of the folding area FDA in the first direction (X-axis direction) may be shorter than the length thereof in the second direction (Y-axis direction). Further, the length of the first non-folding area NFA1 in the first direction (X-axis direction) may be longer than the length of the folding area FDA in the first direction (X-axis direction). The length of the second non-folding area NFA2 in the first direction (X-axis direction) may be longer than the length of the folding area FDA in the first direction (X-axis direction).

The first display area DA1 may be disposed on the front surface of the display device 10. The first display area DA1 may overlap the folding area FDA, the first non-folding area NFA1, and the second non-folding area NFA2. Therefore, when the display device 10 is unfolded, an image may be displayed toward the front side thereof in the folding area FDA, the first non-folding area NFA1, and the second non-folding area NFA2 of the display device 10.

The second display area DA2 may be disposed on the rear surface of the display device 10. The second display area DA2 may overlap the second non-folding area NFA2. Therefore, when the display device 10 is folded, an image may be displayed toward the front side thereof in the second non-folding area NFA2 of the display device 10.

FIGS. 28 and 29 illustrate that a through hole TH having a camera SDA formed therein is disposed in the first non-folding area NFA1, but the present disclosure is not limited thereto. The through hole TH or the camera SDA may be disposed in the second non-folding area NFA2 or the folding area FDA.

Figure 30:
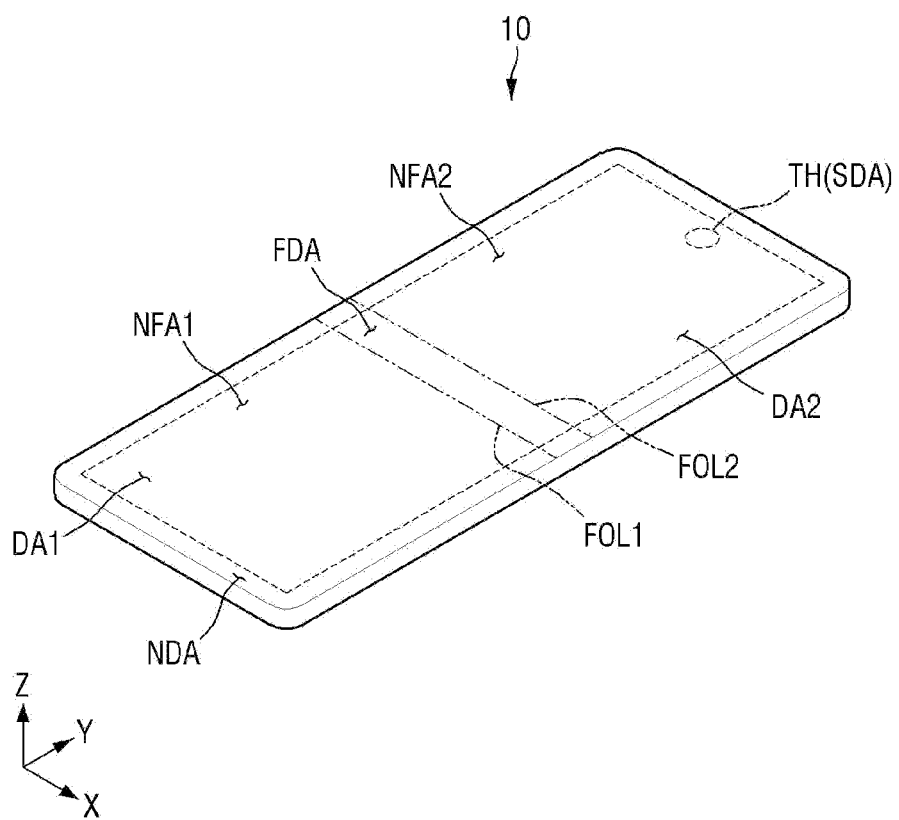
FIGS. 30 and 31 are perspective views illustrating a display device according to an embodiment of the present disclosure.
Figure 31:
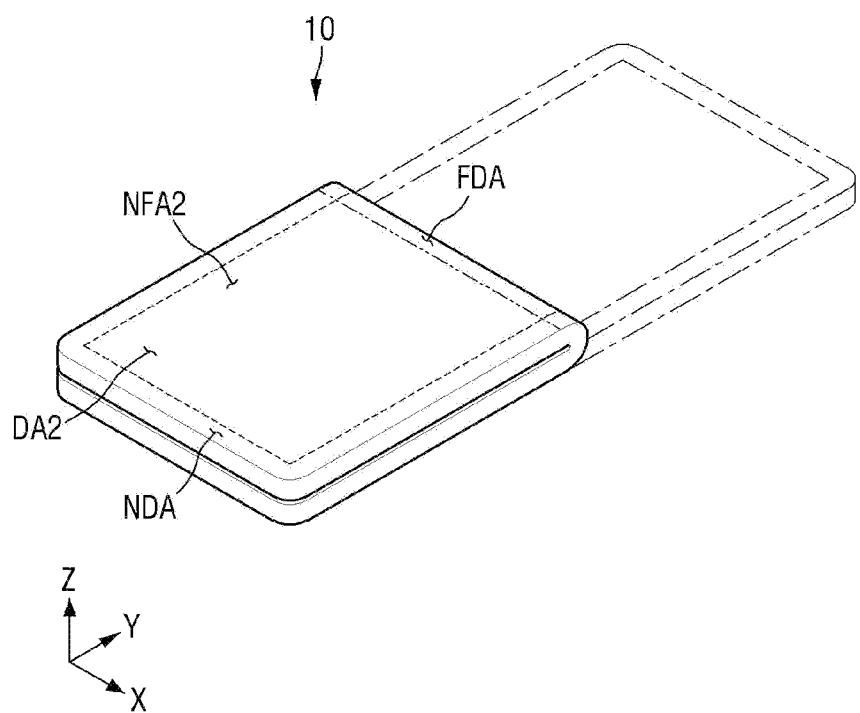

FIGS. 30 and 31 are perspective views illustrating a display device according to an embodiment of the present disclosure.

FIGS. 30 and 31 illustrate the display device 10 as a foldable display device that is folded in the second direction (Y-axis direction). The display device 10 may maintain both a folded state and an unfolded state. The display device 10 may be folded in an in-folding manner in which the front surface is disposed on the inside thereof. When the display device 10 is bent or folded in the in-folding manner, the front surfaces of the display device 10 may be disposed to face each other. Alternatively, the display device 10 may be folded in an out-folding manner in which the front surface is disposed on the outside thereof. When the display device 10 is bent or folded in an out-folding manner, the rear surfaces of the display device 10 may be disposed to face each other.

The display device 10 may include a folding area FDA, the first non-folding area NFA1, and the second non-folding area NFA2. The folding area FDA may be an area in which the display device 10 is folded, and the first and second non-folding areas NFA1 and NFA2 may be areas in which the display device 10 is not folded. The first non-folding area NFA1 may be disposed on one side (e.g., a lower side) of the folding area FDA. The second non-folding area NFA2 may be disposed on the other side (e.g., an upper side) of the folding area FDA.

The touch sensing unit TSU according to an embodiment of the present disclosure may be disposed on each of the first non-folding area NFA1 and the second non-folding area NFA2.

On the other hand, the folding area FDA may be a curved area with a predetermined curvature at a first folding line FOL1 and a second folding line FOL2. Thus, the first folding line FOL1 may be the boundary between the folding area FDA and the first non-folding area NFA1, and the second folding line FOL2 may be the boundary between the folding area FDA and the second non-folding area NFA2.

The first folding line FOL1 and the second folding line FOL2 may extend in the first direction (X-axis direction) as shown in FIGS. 30 and 31. In this case, the display device 10 may be folded in the second direction (Y-axis direction). Accordingly, the length of the display device 10 in the second direction (Y-axis direction) may be reduced to approximately half, so that a user can conveniently carry the display device 10.

However, the extension direction of the first folding line FOL1 and the extension direction of the second folding line FOL2 are not limited to the first direction (X-axis direction). For example, the first folding line FOL1 and the second folding line FOL2 may extend in the second direction (Y-axis direction), and the display device 10 may be folded in the first direction (X-axis direction). In this case, the length of the display device 10 in the first direction (X-axis direction) may be reduced to approximately half. Alternatively, the first folding line FOL1 and the second folding line FOL2 may extend in the diagonal direction of the display device 10 between the first direction (X-axis direction) and the second direction (Y-axis direction). In this case, the display device 10 may be folded in a triangular shape.

When the first folding line FOL1 and the second folding line FOL2 extend in the first direction (X-axis direction) as shown in FIGS. 30 and 31, the length of the folding area FDA in the second direction (Y-axis direction) may be shorter than the length of the folding area FDA in the first direction (X-axis direction). Further, the length of the first non-folding area NFA1 in the second direction (Y-axis direction) may be longer than the length of the folding area FDA in the second direction (Y-axis direction). The length of the second non-folding area NFA2 in the second direction (Y-axis direction) may be longer than the length of the folding area FDA in the second direction (Y-axis direction).

The first display area DA1 may be disposed on the front surface of the display device 10. The first display area DA1 may overlap the folding area FDA, the first non-folding area NFA1, and the second non-folding area NFA2. Therefore, when the display device 10 is unfolded, an image may be displayed toward the front side thereof in the folding area FDA, the first non-folding area NFA1, and the second non-folding area NFA2 of the display device 10.

The second display area DA2 may be disposed on the rear surface of the display device 10. The second display area DA2 may overlap the second non-folding area NFA2. Therefore, when the display device 10 is folded, an image may be displayed toward the front side thereof in the second non-folding area NFA2 of the display device 10.

FIGS. 30 and 31 illustrate that the through hole TH in which the camera SDA or the like is disposed is disposed in the second non-folding area NFA2, but the present disclosure is not limited thereto. The through hole TH may be disposed in the first non-folding area NFA1 or the folding area FDA.

In concluding the detailed description, those skilled in the art will appreciate that many variations and modifications can be made to the embodiments described herein without substantially departing from the principles of the present invention. Therefore, the disclosed embodiments of the invention are used in a generic and descriptive sense only and not for purposes of limitation.

What is claimed is:

1. A display device comprising:
   display pixels comprising light emitting elements arranged in a display area of a display panel and pixel drivers connected to the light emitting elements;
   light sensing pixels comprising light sensing elements arranged in the display area and sensing drivers connected to the light sensing elements;
   a display scan driver configured to sequentially supply display scan signals to the pixel drivers;
   a light sensing driver configured to sequentially supply sensing scan signals to the sensing drivers;
   a pressure sensing unit disposed on the display panel to sense pressure applied at a randomly set position of a touch area of the display panel by a body part of a user to generate a pressure sensing signal;
   a blood pressure detection circuit configured to measure a blood pressure of a user using light sensing signals received from the sensing drivers; and
   a display driving circuit configured to supply control signals to the display scan driver and the light sensing driver to control a light sensing signal detection timing of the light sensing pixels and randomly set the position of the touch area when a mode of the display device is switched to a blood pressure measurement mode, and
   wherein the display driving circuit controls a data driver and the display scan driver such that a preset pressurization information display image is displayed on the display area, and a pressure change according to pressure data based on the pressure sensing signal is displayed as the pressurization information display image in real time.

2. The display device of claim 1, further comprising:
   the pressure sensing unit disposed on one of a rear surface and a front surface of the display panel to sense the pressure applied at the position of the touch area by the body part of the user to generate the pressure sensing signal; and
   a touch driver configured to generate the pressure data and pressure sensing coordinate data according to a change in magnitude of the pressure sensing signal and the position.

3. The display device of claim 1, further comprising:
   a touch sensing unit disposed on the display panel to detect a touch of the user at the position to generate a touch sensing signal; and
   a touch driver configured to generate touch data and touch coordinate data according to the position and a magnitude change of the touch sensing signal.

4. The display device of claim 3, wherein the display driving circuit displays a guide phrase to inform the user of a switch to the blood pressure measurement mode for inducing the user to touch a touch area of the display area, touch sensing signals are received through the touch sensing unit to detect the touch data and the touch coordinate data, and the touch data and the touch coordinate data are transmitted to the display driving circuit in real time.

5. The display device of claim 4, wherein the display driving circuit detects and sets the touch area based on the touch coordinate data, grayscale data preset for blood pressure detection are aligned according to a position of the touch area and supplied to a data driver, and a write control signal is supplied to the display scan driver to control the display pixels of the touch area to emit light, and a light sensing control signal is supplied to the light sensing driver to control the sensing scan signals to be sequentially supplied to the sensing drivers.

6. The display device of claim 5, wherein the display driving circuit supplies coordinate information on the touch area to the blood pressure detection circuit, and the blood pressure detection circuit receives the light sensing signals through each sensing driver corresponding to the touch area based on the coordinate information on the touch area, detects a pulse wave signal from the light sensing signals and calculates blood pressure of the user from the pulse wave signal.

7. The display device of claim 1, wherein among the display pixels of the display area, red, green, and blue display pixels and one light sensing pixel form each unit pixel, and the red, green, and blue display pixels and the one light sensing pixel are alternately arranged in a horizontal or vertical stripe.

8. The display device of claim 7, wherein the display scan driver sequentially supplies display scan signals to the pixel drivers for each horizontal line in response to a write control signal from the display driving circuit, and the light sensing driver sequentially supplies the sensing scan signals to the sensing drivers for each horizontal line in response to a light sensing control signal from the display driving circuit.

9. The display device of claim 8, wherein the mode is switched to the blood pressure measurement mode according to a blood pressure measurement function selection operation or an application execution operation by the user, and when switched to the blood pressure measurement mode, preset video data is supplied to a data driver, and the write control signal is supplied to the display scan driver to display information on the display area indicating the switch to the blood pressure measurement mode.

10. The display device of claim 8, further comprising a touch driver that transmits the pressure data according to a magnitude change of the pressure sensing signal to the display driving circuit.

11. The display device of claim 10, wherein the pressurization information display image is displayed in at least one of a bar block type, a bar gauge type, a circular gauge type, a polygonal figure size type, a polygonal figure gauge type, a polygonal figure block type, a bar graph type, or an arrow gauge type.

12. The display device of claim 8, wherein when the mode is switched to the blood pressure measurement mode, the touch driver receives pressure sensing signals in real time through the pressure sensing unit to detect pressure data and pressure sensing coordinate data, the pressure data and the pressure sensing coordinate data detected in real time are transmitted to the display driving circuit, and the display driving circuit sets a touch area to be touched by the user based on the pressure data and the pressure sensing coordinate data.

13. The display device of claim 12, wherein the display driving circuit supplies coordinate information on the touch area set by the pressure sensing coordinate data to the blood pressure detection circuit, and the blood pressure detection circuit receives the light sensing signals through each sensing driver corresponding to the touch area based on the coordinate information on the touch area, detects a pulse wave signal from the light sensing signals and calculates a blood pressure of the user from the pulse wave signal.

14. A display device comprising:
display pixels comprising light emitting elements arranged in a display area of a display panel and pixel drivers connected to the light emitting elements;
light sensing pixels comprising light sensing elements arranged in the display area and sensing drivers connected to the light sensing elements;
a display scan driver configured to sequentially supply display scan signals to the pixel drivers;
a light sensing driver configured to sequentially supply sensing scan signals to the sensing drivers;
a blood pressure detection circuit configured to measure a blood pressure of a user using light sensing signals received from the sensing drivers; and
a display driving circuit configured to supply control signals to the display scan driver and the light sensing driver to control a light sensing signal detection timing of the light sensing pixels when a mode of the display device is switched to a blood pressure measurement mode,
wherein when the mode is switched to the blood pressure measurement mode, the display driving circuit randomly sets a position of a touch area of the display panel to be touched by the user, and driving timings of a data driver and the display scan driver are controlled to display the randomly set touch area and a preset touch inducing image on the display area.

15. The display device of claim 14, wherein the display driving circuit aligns image data for displaying the touch inducing image according to the randomly set touch area and supplies the image data to the data driver, and a write control signal is supplied to the display scan driver to control the touch area and the preset touch inducing image to be displayed.

16. The display device of claim 14, wherein the display driving circuit aligns grayscale data preset for blood pressure detection in the randomly set touch area according to a position of the touch area and supplies the grayscale data to the data driver, a write control signal is supplied to the display scan driver to control the display pixels of the touch area to emit light, and the light sensing control signal is supplied to the light sensing driver to control the sensing scan signals to be sequentially supplied to the sensing drivers.

17. The display device of claim 16, wherein the display driving circuit supplies coordinate information on the randomly set touch area to the blood pressure detection circuit, and the blood pressure detection circuit receives the light sensing signals through each sensing driver corresponding to the touch area based on the coordinate information on the touch area, detects a pulse wave signal from the light sensing signals, and calculates a blood pressure of the user from the pulse wave signal.

18. A display device comprising:
display pixels comprising light emitting elements arranged in a display area of a display panel and pixel drivers connected to the light emitting elements;
light sensing pixels comprising light sensing elements arranged in the display area and sensing drivers connected to the light sensing elements;
a display scan driver configured to sequentially supply display scan signals to the pixel drivers;

a light sensing driver configured to sequentially supply sensing scan signals to the sensing drivers;
a blood pressure detection circuit configured to measure a blood pressure of a user using light sensing signals received from the sensing drivers; and
a display driving circuit configured to supply control signals to the display scan driver and the light sensing driver to control a light sensing signal detection timing of the light sensing pixels when a mode of the display device is switched to a blood pressure measurement mode,
wherein when the mode is switched to the blood pressure measurement mode, the display driving circuit randomly converts and sets a size of a touch area to be touched by the user and an arrangement position of the touch area, and driving timings of a data driver and the display scan driver are controlled to display boundary lines of the randomly set touch area on the display area.

19. A display device comprising:
display pixels comprising light emitting elements arranged in a display area of a display panel and pixel drivers connected to the light emitting elements;
light sensing pixels comprising light sensing elements arranged in the display area and sensing drivers connected to the light sensing elements;
a display scan driver configured to sequentially supply display scan signals to the pixel drivers;
a light sensing driver configured to sequentially supply sensing scan signals to the sensing drivers;
a blood pressure detection circuit configured to detect a pulse wave signal from light sensing signals received from the sensing drivers and determines time differences between peaks in the pulse wave signal to estimate a blood pressure;
a display driving circuit configured to supply control signals to the display scan driver and the light sensing driver to control a light sensing signal detection timing of the light sensing pixels and randomly set a position of a touch area of the display panel, when a mode of the display device is switched to a blood pressure measurement mode;
a pressure sensing unit disposed on the display panel to sense pressure applied during a touch by a body part of a user on the randomly set position of the touch area of the display panel to generate a pressure sensing signal;
a touch sensing unit disposed on the display panel to detect the touch to generate a touch sensing signal; and
a touch driver configured to generate pressure data, coordinate data, and touch data according to the position, a magnitude change of the pressure sensing signal, and a magnitude change of the touch sensing signal.

20. An electronic device including a display device, the display device comprising:
display pixels comprising light emitting elements arranged in a display area of a display panel and pixel drivers connected to the light emitting elements;
light sensing pixels comprising light sensing elements arranged in the display area and sensing drivers connected to the light sensing elements;
a display scan driver configured to sequentially supply display scan signals to the pixel drivers;
a light sensing driver configured to sequentially supply sensing scan signals to the sensing drivers;
a pressure sensing unit disposed on the display panel to sense pressure applied at a randomly set position of a touch area of the display panel by a body part of the user to generate a pressure sensing signal;
a blood pressure detection circuit configured to measure a blood pressure of a user using light sensing signals received from the sensing drivers; and
a display driving circuit configured to supply control signals to the display scan driver and the light sensing driver to control a light sensing signal detection timing of the light sensing pixels and randomly set the position of the touch area when a mode of the display device is switched to a blood pressure measurement mode, and
wherein the display driving circuit controls a data driver and the display scan driver such that a preset pressurization information display image is displayed on the display area, and a pressure change according to pressure data based on the pressure sensing signal is displayed as the pressurization information display image in real time.

* * * * *